United States Patent
Kaufman et al.

(10) Patent No.: US 7,260,248 B2
(45) Date of Patent: Aug. 21, 2007

(54) IMAGE PROCESSING USING MEASURES OF SIMILARITY

(75) Inventors: Howard Kaufman, Newton, MA (US); Philippe Schmid, Lausanne (CH)

(73) Assignee: MediSpectra, Inc., Lexington, MA (US)

( * ) Notice: Subject to any disclaimer, the term of this patent is extended or adjusted under 35 U.S.C. 154(b) by 791 days.

(21) Appl. No.: 10/099,881

(22) Filed: Mar. 15, 2002

(65) Prior Publication Data

US 2003/0144585 A1    Jul. 31, 2003

Related U.S. Application Data

(63) Continuation-in-part of application No. 10/068,133, filed on Feb. 5, 2002, which is a continuation of application No. 09/738,614, filed on Dec. 15, 2000.

(60) Provisional application No. 60/353,978, filed on Jan. 31, 2002, provisional application No. 60/170,972, filed on Dec. 15, 1999.

(51) Int. Cl.
  *G06K 9/00* (2006.01)
(52) U.S. Cl. ...................... 382/128; 382/212
(58) Field of Classification Search ............... 382/209, 382/173, 128, 133, 212; 600/407, 476, 431
  See application file for complete search history.

(56) References Cited

U.S. PATENT DOCUMENTS

| 3,013,467 | A | 12/1961 | Minsky ........................... 88/14 |
| 3,632,865 | A | 1/1972 | Haskell et al. ................ 178/6 |
| 3,809,072 | A | 5/1974 | Ersek et al. ................... 128/23 |
| 3,890,462 | A | 6/1975 | Limb et al. ................... 178/6.8 |
| 3,945,371 | A | 3/1976 | Adelman |
| 3,963,019 | A | 6/1976 | Quandt et al. ................. 128/2 |
| D242,393 | S | 11/1976 | Bauman ................... D83/12 R |
| D242,396 | S | 11/1976 | Bauman ................... D83/12 R |
| D242,397 | S | 11/1976 | Bauman ................... D83/12 R |
| D242,398 | S | 11/1976 | Bauman ................... D83/12 R |
| 4,017,192 | A | 4/1977 | Rosenthal .................... 356/201 |
| 4,071,020 | A | 1/1978 | Puglise et al. .................. 128/2 |
| 4,198,571 | A | 4/1980 | Sheppard .................... 250/571 |

(Continued)

FOREIGN PATENT DOCUMENTS

DE    196 29 646    1/1988

(Continued)

OTHER PUBLICATIONS

Noble et al., "Automated, Nonrigid Alignment of Clinical Myocardial Contrast Echocardiography Image Sequences: Comparison with Manual Alignm'ent," *Ultrasound in Medicine and Biology*, vol. 28, No. 1 (2002), pp. 115-123.

(Continued)

*Primary Examiner*—Samir Ahmed
*Assistant Examiner*—ONeal R. Mistry
(74) *Attorney, Agent, or Firm*—Goodwin Procter LLP

(57) ABSTRACT

The invention provides methods of relating a plurality of images based on measures of similarity. The methods of the invention are useful in the segmentation of a sequence of colposcopic images of tissue, for example. The methods may be applied in the determination of tissue characteristics in acetowhitening testing of cervical tissue, for example.

34 Claims, 26 Drawing Sheets
(16 of 26 Drawing Sheet(s) Filed in Color)

U.S. PATENT DOCUMENTS

| Patent | | Date | Inventor | Class |
|---|---|---|---|---|
| 4,218,703 | A | 8/1980 | Netravali et al. | 358/136 |
| 4,254,421 | A | 3/1981 | Kreutel, Jr. | 343/754 |
| 4,273,110 | A | 6/1981 | Groux | 128/6 |
| 4,349,510 | A | 9/1982 | Kolehmainen et al. | |
| 4,357,075 | A | 11/1982 | Hunter | 350/294 |
| 4,396,579 | A | 8/1983 | Schroeder et al. | |
| 4,397,557 | A | 8/1983 | Herwig et al. | 356/342 |
| 4,515,165 | A | 5/1985 | Carroll | 128/664 |
| 4,549,229 | A | 10/1985 | Nakano et al. | 360/8 |
| 4,558,462 | A | 12/1985 | Horiba et al. | 382/42 |
| 4,641,352 | A | 2/1987 | Fenster et al. | 382/6 |
| 4,646,722 | A | 3/1987 | Silverstein et al. | 128/4 |
| 4,662,360 | A | 5/1987 | O'Hara et al. | 128/9 |
| 4,733,063 | A | 3/1988 | Kimura et al. | 250/201 |
| 4,741,326 | A | 5/1988 | Sidall et al. | 128/4 |
| 4,753,530 | A | 6/1988 | Knight et al. | 356/73 |
| 4,755,055 | A | 7/1988 | Johnson et al. | |
| 4,768,513 | A | 9/1988 | Suzuki | 128/634 |
| 4,800,571 | A | 1/1989 | Konishi | 375/10 |
| 4,803,049 | A | 2/1989 | Hirschfeld et al. | |
| 4,844,617 | A | 7/1989 | Kelderman et al. | 356/372 |
| 4,845,352 | A | 7/1989 | Benschop | 250/201 |
| 4,852,955 | A | 8/1989 | Doyle et al. | 350/1.2 |
| 4,877,033 | A | 10/1989 | Seitz, Jr. | 128/660.05 |
| 4,878,485 | A | 11/1989 | Adair | 128/6 |
| 4,891,829 | A | 1/1990 | Deckman et al. | 378/4 |
| 4,930,516 | A | 6/1990 | Alfano et al. | 128/665 |
| 4,945,478 | A | 7/1990 | Merickel et al. | 364/413.22 |
| 4,965,441 | A | 10/1990 | Picard | 250/201.3 |
| 4,972,258 | A | 11/1990 | Wolf et al. | 358/93 |
| 4,974,580 | A | 12/1990 | Anapliotis | 128/4 |
| 4,979,498 | A | 12/1990 | Oneda et al. | 128/6 |
| 4,997,242 | A | 3/1991 | Amos | 350/6.91 |
| 5,003,979 | A | 4/1991 | Merickel et al. | 364/413.22 |
| 5,011,243 | A | 4/1991 | Doyle et al. | 350/1.2 |
| 5,022,757 | A | 6/1991 | Modell | 356/318 |
| 5,028,802 | A | 7/1991 | Webb et al. | 250/571 |
| 5,032,720 | A | 7/1991 | White | 250/236 |
| 5,034,613 | A | 7/1991 | Denk et al. | 250/458.1 |
| 5,036,853 | A | 8/1991 | Jeffcoat et al. | 128/634 |
| 5,042,494 | A | 8/1991 | Alfano | 128/665 |
| 5,048,946 | A | 9/1991 | Sklar et al. | 351/206 |
| 5,054,926 | A | 10/1991 | Dabbs et al. | 356/345 |
| 5,065,008 | A | 11/1991 | Hakamata et al. | 250/216 |
| 5,071,246 | A | 12/1991 | Blaha et al. | 351/221 |
| 5,074,306 | A | 12/1991 | Green et al. | 128/664 |
| 5,083,220 | A | 1/1992 | Hill | 359/234 |
| 5,091,652 | A | 2/1992 | Mathies et al. | 250/458.1 |
| 5,101,825 | A | 4/1992 | Gravenstein et al. | 128/633 |
| 5,120,953 | A | 6/1992 | Harris | 250/227.2 |
| 5,122,653 | A | 6/1992 | Ohki | 250/216 |
| 5,132,526 | A | 7/1992 | Iwasaki | 250/201.3 |
| 5,139,025 | A | 8/1992 | Lewis et al. | 128/665 |
| 5,154,166 | A | 10/1992 | Chikama | 128/4 |
| 5,159,919 | A | 11/1992 | Chikama | 128/4 |
| 5,161,053 | A | 11/1992 | Dabbs | 359/384 |
| 5,162,641 | A | 11/1992 | Fountain | 250/201.2 |
| 5,162,941 | A | 11/1992 | Favro et al. | 359/386 |
| 5,168,157 | A | 12/1992 | Kimura | 250/234 |
| 5,192,980 | A | 3/1993 | Dixon et al. | 356/326 |
| 5,193,525 | A | 3/1993 | Silverstein et al. | 128/4 |
| RE34,214 | E | 4/1993 | Carlsson et al. | 358/93 |
| 5,199,431 | A | 4/1993 | Kittrell et al. | 128/634 |
| 5,201,318 | A | 4/1993 | Rava et al. | 128/665 |
| 5,201,908 | A | 4/1993 | Jones | 128/4 |
| 5,203,328 | A | 4/1993 | Samuels et al. | 128/633 |
| 5,205,291 | A | 4/1993 | Potter | |
| 5,225,671 | A | 7/1993 | Fukuyama | 250/216 |
| 5,235,457 | A | 8/1993 | Lichtman et al. | 359/368 |
| 5,237,984 | A | 8/1993 | Williams, III et al. | 128/4 |
| 5,239,178 | A | 8/1993 | Derndinger et al. | 250/234 |
| 5,248,876 | A | 9/1993 | Kerstens et al. | 250/561 |
| 5,253,071 | A | 10/1993 | MacKay | 358/222 |
| 5,257,617 | A | 11/1993 | Takahashi | 128/4 |
| 5,260,569 | A | 11/1993 | Kimura | 250/234 |
| 5,260,578 | A | 11/1993 | Bliton et al. | 250/461.1 |
| 5,261,410 | A | 11/1993 | Alfano et al. | 128/664 |
| 5,262,646 | A | 11/1993 | Booker et al. | 250/341 |
| 5,267,179 | A * | 11/1993 | Butler et al. | 382/212 |
| 5,274,240 | A | 12/1993 | Mathies et al. | 250/458.1 |
| 5,284,149 | A | 2/1994 | Dhadwal et al. | 128/665 |
| 5,285,490 | A * | 2/1994 | Bunch et al. | 378/156 |
| 5,286,964 | A | 2/1994 | Fountain | 250/201.2 |
| 5,289,274 | A | 2/1994 | Kondo | 348/208 |
| 5,294,799 | A | 3/1994 | Aslund et al. | 250/458.1 |
| 5,296,700 | A | 3/1994 | Kumagai | 250/216 |
| 5,303,026 | A | 4/1994 | Strobl et al. | 356/318 |
| 5,306,902 | A | 4/1994 | Goodman | 250/201.3 |
| 5,313,567 | A | 5/1994 | Civanlar et al. | 395/124 |
| 5,319,200 | A | 6/1994 | Rosenthal et al. | 250/341 |
| 5,321,501 | A | 6/1994 | Swanson et al. | 356/345 |
| 5,324,979 | A | 6/1994 | Rosenthal | 250/504 R |
| 5,325,846 | A | 7/1994 | Szabo | 128/4 |
| 5,329,352 | A | 7/1994 | Jacobsen | 356/301 |
| 5,337,734 | A | 8/1994 | Saab | 128/4 |
| 5,343,038 | A | 8/1994 | Nishiwaki et al. | 250/234 |
| 5,345,306 | A | 9/1994 | Ichimura et al. | 356/346 |
| 5,345,941 | A | 9/1994 | Rava et al. | 128/665 |
| 5,349,961 | A | 9/1994 | Stoddart et al. | 128/665 |
| 5,383,874 | A | 1/1995 | Jackson et al. | |
| 5,398,685 | A | 3/1995 | Wilk et al. | 128/653.1 |
| 5,402,768 | A | 4/1995 | Adair | 128/4 |
| 5,406,939 | A | 4/1995 | Bala | 128/4 |
| 5,412,563 | A | 5/1995 | Cline et al. | |
| 5,413,092 | A | 5/1995 | Williams, III et al. | 128/4 |
| 5,413,108 | A | 5/1995 | Alfano | 128/665 |
| 5,415,157 | A | 5/1995 | Welcome | 128/4 |
| 5,418,797 | A | 5/1995 | Bashkansky et al. | 372/3 |
| 5,419,311 | A | 5/1995 | Yabe et al. | 128/4 |
| 5,419,323 | A | 5/1995 | Kittrell et al. | 128/653 |
| 5,421,337 | A | 6/1995 | Richards-Kortum et al. | 128/665 |
| 5,421,339 | A | 6/1995 | Ramanujam et al. | 128/665 |
| 5,424,543 | A | 6/1995 | Dombrowski et al. | 250/330 |
| 5,441,053 | A | 8/1995 | Lodder et al. | |
| 5,450,857 | A | 9/1995 | Garfield et al. | 128/778 |
| 5,451,931 | A | 9/1995 | Miller et al. | 340/630 |
| 5,452,723 | A | 9/1995 | Wu et al. | |
| 5,458,132 | A | 10/1995 | Yabe et al. | 128/4 |
| 5,458,133 | A | 10/1995 | Yabe et al. | 600/121 |
| 5,467,767 | A | 11/1995 | Alfano et al. | 128/665 |
| 5,469,853 | A | 11/1995 | Law et al. | 128/662.06 |
| 5,477,382 | A | 12/1995 | Pernick | 359/559 |
| 5,480,775 | A | 1/1996 | Ito et al. | 435/7.2 |
| 5,493,444 | A | 2/1996 | Khoury et al. | 359/559 |
| 5,496,259 | A | 3/1996 | Perkins | 600/124 |
| 5,507,295 | A | 4/1996 | Skidmore | 600/121 |
| 5,516,010 | A | 5/1996 | O'Hara et al. | 600/122 |
| 5,519,545 | A | 5/1996 | Kawahara | 360/46 |
| 5,529,235 | A | 6/1996 | Bolarski et al. | 227/175.1 |
| 5,536,236 | A | 7/1996 | Yabe et al. | 600/125 |
| 5,545,121 | A | 8/1996 | Yabe et al. | 600/121 |
| 5,551,945 | A | 9/1996 | Yabe et al. | 600/122 |
| 5,556,367 | A | 9/1996 | Yabe et al. | 600/124 |
| 5,562,100 | A | 10/1996 | Kittrell et al. | 128/665 |
| 5,579,773 | A | 12/1996 | Vo-Dinh et al. | 128/665 |
| 5,582,168 | A | 12/1996 | Samuels et al. | 128/633 |
| 5,587,832 | A | 12/1996 | Krause | 359/385 |
| 5,596,992 | A | 1/1997 | Haaland et al. | 128/664 |
| 5,599,717 | A | 2/1997 | Vo-Dinh | 436/63 |
| 5,609,560 | A | 3/1997 | Ichikawa et al. | 600/101 |
| 5,612,540 | A | 3/1997 | Richards-Korum et al. | 250/461.2 |
| 5,623,932 | A | 4/1997 | Ramanujam et al. | 128/665 |

| Patent No. | Kind | Date | Inventor | Class |
|---|---|---|---|---|
| 5,643,175 | A | 7/1997 | Adair | 600/133 |
| 5,647,368 | A | 7/1997 | Zeng et al. | 128/665 |
| 5,659,384 | A | 8/1997 | Ina | 355/53 |
| 5,662,588 | A | 9/1997 | Lida | 600/121 |
| 5,685,822 | A | 11/1997 | Harhen | 600/125 |
| 5,690,106 | A | 11/1997 | Bani-Hashemi et al. | 128/653.1 |
| 5,693,043 | A | 12/1997 | Kittrell et al. | 606/15 |
| 5,695,448 | A | 12/1997 | Kimura et al. | 600/121 |
| 5,697,373 | A | 12/1997 | Richards-Kortum et al. | 128/664 |
| 5,699,795 | A | 12/1997 | Richards-Kortum | 128/634 |
| 5,704,892 | A | 1/1998 | Adair | 600/121 |
| 5,707,343 | A | 1/1998 | O'Hara et al. | 600/121 |
| 5,713,364 | A | 2/1998 | DeBaryshe et al. | 128/664 |
| 5,717,209 | A | 2/1998 | Bigman et al. | 250/339.12 |
| 5,730,701 | A | 3/1998 | Furukawa et al. | 600/127 |
| 5,733,244 | A | 3/1998 | Yasui et al. | 600/127 |
| 5,735,276 | A | 4/1998 | Lemelson et al. | 128/653 |
| 5,746,695 | A | 5/1998 | Yasui et al. | 600/127 |
| 5,768,333 | A | 6/1998 | Abdel-Mottaleb | 378/37 |
| 5,769,792 | A | 6/1998 | Palcic et al. | 600/477 |
| 5,773,835 | A | 6/1998 | Sinofsky et al. | 250/462.1 |
| 5,784,162 | A | 7/1998 | Cabib et al. | |
| 5,791,346 | A | 8/1998 | Craine et al. | 128/653 |
| 5,795,632 | A | 8/1998 | Buchalter | 428/35.2 |
| 5,800,350 | A | 9/1998 | Coppleson et al. | 600/372 |
| 5,807,248 | A | 9/1998 | Mills | 600/322 |
| 5,813,987 | A | 9/1998 | Modell et al. | 600/473 |
| 5,817,015 | A | 10/1998 | Adair | 600/121 |
| 5,830,146 | A | 11/1998 | Skladnev et al. | 600/478 |
| 5,832,931 | A | 11/1998 | Wachter et al. | |
| 5,833,617 | A | 11/1998 | Hayashi | 600/476 |
| 5,838,435 | A | 11/1998 | Sandison | |
| 5,840,035 | A | 11/1998 | Heusmann et al. | 600/47 |
| 5,842,995 | A | 12/1998 | Mahadevan-Jansen et al. | 600/473 |
| 5,855,551 | A | 1/1999 | Sklandnev et al. | 600/372 |
| 5,860,913 | A | 1/1999 | Yamaya et al. | 600/127 |
| 5,863,287 | A | 1/1999 | Segawa | 600/121 |
| 5,865,726 | A | 2/1999 | Katsurada et al. | 600/127 |
| 5,871,439 | A | 2/1999 | Takahashi et al. | |
| 5,876,329 | A | 3/1999 | Harhen | 600/125 |
| 5,894,340 | A | 4/1999 | Loree et al. | |
| 5,902,246 | A | 5/1999 | McHenry et al. | |
| 5,912,257 | A | 6/1999 | Prasad et al. | |
| 5,920,399 | A | 7/1999 | Sandison et al. | 356/418 |
| 5,921,926 | A | 7/1999 | Rolland et al. | 600/407 |
| 5,929,985 | A | 7/1999 | Sandison et al. | 365/318 |
| 5,931,779 | A | 8/1999 | Arakaki et al. | 600/310 |
| 5,938,617 | A | 8/1999 | Vo-Dinh | 600/476 |
| 5,941,834 | A | 8/1999 | Skladnev et al. | 600/587 |
| 5,983,125 | A | 11/1999 | Alfano et al. | 600/473 |
| 5,987,343 | A | 11/1999 | Kinast | |
| 5,989,184 | A | 11/1999 | Blair | 600/167 |
| 5,991,653 | A | 11/1999 | Richards-Kortum et al. | 660/475 |
| 5,995,645 | A * | 11/1999 | Soenksen et al. | 382/133 |
| 5,999,844 | A | 12/1999 | Gombrich et al. | |
| 6,011,596 | A * | 1/2000 | Burl et al. | 348/699 |
| 6,021,344 | A | 2/2000 | Lui et al. | 600/476 |
| 6,026,319 | A | 2/2000 | Hayashi | |
| 6,058,322 | A * | 5/2000 | Nishikawa et al. | 600/408 |
| 6,067,371 | A | 5/2000 | Gouge et al. | |
| 6,069,689 | A | 5/2000 | Zeng et al. | 356/773 |
| 6,083,487 | A | 7/2000 | Biel | 424/9.6 |
| 6,091,985 | A | 7/2000 | Alfano et al. | 600/476 |
| 6,092,722 | A | 7/2000 | Heinrichs et al. | |
| 6,095,982 | A | 8/2000 | Richards-Kortum et al. | 600/476 |
| 6,096,065 | A | 8/2000 | Crowley | 607/88 |
| 6,099,464 | A | 8/2000 | Shimizu et al. | 600/104 |
| 6,101,408 | A * | 8/2000 | Craine et al. | 600/425 |
| 6,104,945 | A | 8/2000 | Modell et al. | 600/473 |
| 6,119,031 | A | 9/2000 | Crowley | 600/407 |
| 6,123,454 | A | 9/2000 | Canfield et al. | |
| 6,124,597 | A | 9/2000 | Shehada et al. | 250/461.2 |
| 6,126,899 | A * | 10/2000 | Woudenberg et al. | 422/50 |
| 6,135,965 | A | 10/2000 | Tumor et al. | |
| 6,146,897 | A | 11/2000 | Cohenford et al. | 436/63 |
| 6,166,079 | A | 12/2000 | Follen et al. | |
| 6,169,817 | B1 | 1/2001 | Parker et al. | 382/131 |
| 6,187,289 | B1 | 2/2001 | Richards-Kortum et al. | 424/9.8 |
| 6,208,887 | B1 | 3/2001 | Clarke et al. | 600/476 |
| 6,210,331 | B1 | 4/2001 | Raz | |
| 6,224,256 | B1 | 5/2001 | Bala | |
| 6,241,662 | B1 | 6/2001 | Richards-Kortum et al. | 600/310 |
| 6,243,601 | B1 | 6/2001 | Wist | 600/473 |
| 6,246,471 | B1 | 6/2001 | Jung et al. | 356/73 |
| 6,246,479 | B1 | 6/2001 | Jung et al. | 356/419 |
| 6,258,576 | B1 | 7/2001 | Richards-Kortum et al. | 435/172 |
| 6,277,067 | B1 * | 8/2001 | Blair | 600/167 |
| 6,285,639 | B1 | 9/2001 | Maenza et al. | 369/47.28 |
| 6,289,236 | B1 | 9/2001 | Koenig et al. | |
| 6,312,385 | B1 | 11/2001 | Mo et al. | 600/443 |
| 6,317,617 | B1 | 11/2001 | Gilhuijs et al. | 600/408 |
| 6,332,092 | B1 | 12/2001 | Deckert et al. | |
| D453,832 | S | 2/2002 | Morrell et al. | D24/138 |
| D453,962 | S | 2/2002 | Morrell et al. | D42/138 |
| D453,963 | S | 2/2002 | Morrell et al. | D24/138 |
| D453,964 | S | 2/2002 | Morrell et al. | D24/138 |
| 6,370,422 | B1 | 4/2002 | Richards-Kortum et al. | |
| 6,373,998 | B2 * | 4/2002 | Thirion et al. | 382/294 |
| 6,377,842 | B1 | 4/2002 | Pogue et al. | 600/478 |
| 6,385,484 | B2 | 5/2002 | Nordstrom et al. | 600/476 |
| 6,390,671 | B1 | 5/2002 | Tseng | |
| 6,405,070 | B1 | 6/2002 | Banerjee | |
| 6,411,835 | B1 | 6/2002 | Modell et al. | 600/407 |
| 6,411,838 | B1 | 6/2002 | Nordstrom et al. | 600/476 |
| D460,821 | S | 7/2002 | Morrell et al. | D24/138 |
| 6,421,553 | B1 | 7/2002 | Costa et al. | 600/476 |
| 6,424,852 | B1 | 7/2002 | Zavislan | |
| 6,427,082 | B1 | 7/2002 | Nordstrom et al. | 600/476 |
| 6,465,968 | B1 * | 10/2002 | Sendai | 315/169.3 |
| 6,466,687 | B1 * | 10/2002 | Uppaluri et al. | 382/128 |
| 6,487,440 | B2 | 11/2002 | Deckert et al. | |
| 6,497,659 | B1 | 12/2002 | Rafert | |
| 6,571,118 | B1 | 5/2003 | Utzinger et al. | 600/476 |
| 6,571,119 | B2 | 5/2003 | Hayashi | |
| 6,574,502 | B2 | 6/2003 | Hayashi | 600/476 |
| 6,593,101 | B2 | 7/2003 | Richards-Kortum et al. | |
| 6,593,102 | B2 | 7/2003 | Zahniser | |
| 6,633,657 | B1 * | 10/2003 | Kump et al. | 382/128 |
| 6,639,674 | B2 | 10/2003 | Sokolov et al. | |
| 6,640,000 | B1 * | 10/2003 | Fey et al. | 382/128 |
| 6,671,540 | B1 * | 12/2003 | Hochman | 600/431 |
| 6,697,666 | B1 | 2/2004 | Richards-Kortum et al. | |
| 6,717,668 | B2 * | 4/2004 | Treado et al. | 356/327 |
| 6,760,613 | B2 | 7/2004 | Nordstrom et al. | |
| 6,766,184 | B2 * | 7/2004 | Utzinger et al. | 600/407 |
| 6,768,918 | B2 | 7/2004 | Zelenchuk | 600/476 |
| 6,794,431 | B1 | 9/2004 | Rosania et al. | |
| 6,818,903 | B2 | 11/2004 | Schomacker et al. | |
| 6,826,422 | B1 | 11/2004 | Modell et al. | |
| D500,134 | S | 12/2004 | Banks et al. | |
| 6,839,661 | B2 | 1/2005 | Costa et al. | |
| 6,847,490 | B1 | 1/2005 | Nordstrom et al. | |
| 6,902,935 | B2 | 6/2005 | Kaufman et al. | |
| D507,349 | S | 7/2005 | Banks et al. | |
| 6,933,154 | B2 | 8/2005 | Schomacker et al. | |
| 6,975,899 | B2 | 12/2005 | Faupel et al. | |
| 2001/0041843 | A1 | 11/2001 | Modell et al. | |
| 2002/0007122 | A1 | 1/2002 | Kaufman et al. | 600/476 |
| 2002/0007123 | A1 * | 1/2002 | Balas | 600/476 |
| 2002/0107668 | A1 | 8/2002 | Costa et al. | 702/189 |

| | | | |
|---|---|---|---|
| 2002/0127735 | A1 | 9/2002 | Kaufman et al. .......... 600/436 |
| 2002/0133073 | A1 | 9/2002 | Nordstrom et al. |
| 2002/0177777 | A1 | 11/2002 | Nordstrom et al. ......... 600/475 |
| 2002/0183626 | A1 | 12/2002 | Nordstrom et al. ......... 600/476 |
| 2002/0197728 | A1 | 12/2002 | Kaufman et al. |
| 2003/0095721 | A1 | 5/2003 | Clune et al. ................ 382/294 |
| 2003/0114762 | A1 | 6/2003 | Balas et al. |
| 2003/0144585 | A1 | 7/2003 | Kaufman et al. .......... 600/407 |
| 2003/0163049 | A1 | 8/2003 | Balas |
| 2003/0207250 | A1 | 11/2003 | Kaufman et al. |
| 2004/0007674 | A1 | 1/2004 | Schomacker et al. .... 250/458.1 |
| 2004/0010187 | A1 | 1/2004 | Schomacker et al. ....... 600/317 |
| 2004/0010195 | A1 | 1/2004 | Zelenchuk |
| 2004/0010375 | A1 | 1/2004 | Schomacker et al. |
| 2004/0023406 | A1 | 2/2004 | Schomacker et al. ....... 436/164 |
| 2004/0206882 | A1 | 10/2004 | Banks et al. |
| 2004/0206913 | A1 | 10/2004 | Costa et al. |
| 2004/0206914 | A1 | 10/2004 | Schomacker et al. |
| 2004/0207625 | A1 | 10/2004 | Griffin et al. |
| 2004/0208385 | A1 | 10/2004 | Jiang |
| 2004/0208390 | A1 | 10/2004 | Jiang et al. |
| 2004/0209237 | A1 | 10/2004 | Flewelling et al. |
| 2005/0054936 | A1 | 3/2005 | Balas |
| 2005/0090751 | A1 | 4/2005 | Balas |

FOREIGN PATENT DOCUMENTS

| | | |
|---|---|---|
| EP | 0 135 134 | 3/1985 |
| EP | 0 280 418 | 8/1988 |
| EP | 0 335 725 | 10/1989 |
| EP | 0 444 689 A2 | 9/1991 |
| EP | 0 474 264 | 3/1992 |
| EP | 0 641 542 | 3/1995 |
| EP | 0 689 045 A1 | 12/1995 |
| EP | 0 737 849 A2 | 10/1996 |
| EP | 1246124 A2 | 10/2002 |
| JP | 1-245215 | 9/1989 |
| JP | 2-17429 | 1/1990 |
| JP | 5-256772 | 10/1993 |
| JP | 08-280602 | 10/1996 |
| SU | 1 223 092 A | 4/1986 |
| WO | WO92/19148 | 11/1992 |
| WO | WO93/14688 | 8/1993 |
| WO | WO94/26168 | 11/1994 |
| WO | WO95/00067 | 1/1995 |
| WO | WO95/04385 | 2/1995 |
| WO | 96/41152 | 12/1996 |
| WO | WO97/05473 | 2/1997 |
| WO | WO98/30889 | 2/1997 |
| WO | WO97/48331 | 12/1997 |
| WO | WO98/05253 | 2/1998 |
| WO | WO98/24369 | 6/1998 |
| WO | WO98/41176 | 9/1998 |
| WO | WO99/18847 | 4/1999 |
| WO | WO99/20313 | 4/1999 |
| WO | WO99/20314 | 4/1999 |
| WO | WO99/47041 | 9/1999 |
| WO | WO99/57507 | 11/1999 |
| WO | WO99/57529 | 11/1999 |
| WO | WO 00/15101 | 3/2000 |
| WO | WO 00/41615 | 7/2000 |
| WO | WO 00/57361 | 9/2000 |
| WO | WO 00/59366 | 10/2000 |
| WO | WO 00/74556 | 12/2000 |
| WO | 3063706 | 8/2003 |
| WO | 04/005885 | 1/2004 |
| WO | 04/005895 | 1/2004 |
| WO | 04/095359 | 11/2004 |

OTHER PUBLICATIONS

Ko et al., "Multiresolution Registration of Coronary Artery Image Sequences," *International Journal of Medical Informatics*, vol. 44 (1997), pp. 93-104.

International Search Report for International Application No. PCT/US03/03007 dated Jun. 26, 2003 (1 pg.).
Fielding et al., "Prediction of Outcome After Curative Resection for Large Bowel Cancer," *The Lancet*, Oct. 18, 1986, pp. 904-907.
Lin et al., "Evidence of possible carcinogenesis during conformational changes in bladder mucosa induced by bladder outlet obstruction," Cancer Letters, 79 (1994), 221-226.
Zhao, Project Abstract, "Integration of 3-D Imaging Technology and Feature Extraction Algorithm Designs," Center for Engineering Education and Practice, University of Michigan—Dearborn, Feb. 1999.
Agrawal et al. (1999), "Fluorescence Spectroscopy of the Cervix: Influence of Acetic Acid, Cervical Mucus, and Vaginal Medications," *Lasers in Surgery and Medicine*, 25:237-249.
Althof et al. (1997), "A rapid and automatic image registration algorithm with subpixel accuracy," *IEEE Transactions on Medical Imaging*, 16(3):308-316.
Anderson (1994), "Confocal Laser Microscopes See A Wider Field of Application", *Laser Focus World*, pp. 83-86.
Aström et al. (1999), "Motion estimation in image sequences using the deformation of apparent contours," *IEEE Transactions on Pattern Analysis and Machine Intelligence*, 21(2):114-127.
Balakrishnama et al, "Linear Discriminant Analysis—A Brief Tutorial," *Institute for Signal and Information Processing Department of Electrical and Computer Engineering*, 8 pages.
Balas (1997), "An Imaging Colorimeter for Noncontact Tissue Color Mapping," *IEEE Transactions on Biomedical Engineering*, 44(6):468-474.
Balas (2001), "A Novel Optical Imaging Method for the Early Detection, Quantitative Grading, and Mapping of Cancerous and Precancerous Lesions of Cervix," *IEEE Transactions on Biomedical Engineering*, 48(1):96-104.
Balas et al. (1997), "A modular diffuse reflection and fluorescence emission imaging colorimeter for the in-vivo study of parameters related with the phototoxic effect in PDT," *SPIE*, 3191:50-57.
Balas et al. (1998), "In Vivo Assessment of Acetic Acid-Cervical Tissue Interaction Using Quantitative Imaging of Back-Scattered Light: Its Potential Use for the In Vivo Cervical Cancer Detection Grading and Mapping," Part of EUROPTO Conference on Optical Biopsy, Stockholm, Sweden, *SPIE*, vol. 3568:31-37.
Balas et al. (1999), "In Vivo Detection and Staging of Epithelial Dysplasias and Malignancies Based on the Quantitative Assessment of Acetic Acid-Tissue Interaction Kinetics," *Journal of Photochemistry and Photobiology B: Biology*, 53:153-157.
Bessey et al. (1949), "The Fluorometric measurement of the nucleotides of riboflavin and their concentration in tissues," *J. Biol.-Chem.*; 180:755-769.
Bors et al. (1998), "Optical flow estimation and moving object segmentation based on median radial basis function network," *IEEE Transactions on Image Processing*, 7(5);693-702.
Bouthemy et al. (1999), "A unified approach to shot change detection and camera motion characterization," *IEEE Transactions on Circuits and Systems for Video Technology*, 9(7):1030-1044.
Braichotte et al. (1995), "Clinical Pharmacokinetic Studies of Photofrin by Fluorescence Spectroscopy in the Oral Cavity, the Esophagus, and the Bronchi," *Cancer* 75(11):2760-2778.
Brown (1990), "Chemometrics," *Anal. Chem.*, 62:84R-101R.
Camus et al. (1997), "Real-time quantized optical flow," *Real-Time Imaging*, 3:71-86.
Caplier et al. (1998), "Real-time implementation of a MRF-based motion detection algorithm," *Real-Time Imaging*, 4:41-54.
Contini et al. (1989), "Colposcopy and Computer Graphics: a New Method?" *Amer. J. Obstet. Gynecol.*, 160(3):535-538.
Craine et al. (1993), "Digital Imaging Colposcopy: basic concepts and applications," *Amer. J. Obstet. Gynecol.*, 82(5):869-873.
Craine et al. (1998), "Digital imaging colposcopy: Corrected area measurements using shape-from-shading," *IEEE Transactions on Medical Imaging*, 17(6):1003-1010.
Crisp et al. (1990), "The Computerized Digital Imaging Colposcope: Future Directions," *Amer. J. Obstet. Gynecol.*, 162(6):1491-1497.
Cronjé et al. (1997), "Effects of Dilute Acetic Acid on the Cervical Smear," *Acta. Cytol.*, 41:1091-1094.

Davidovits et al. (1971), "Scanning Laser Microscope for Biological Investigations", *Applied Optics*, 10(7):1615-1619.

Dickman et al. (2001), "Identification of Cervical Neoplasia Using a Simulation of Human Vision," *Journal of Lower Genital Tract Disease*, 5(3):144-152.

Drezek et al. (1999), "Light scattering from cells: finite-difference time-domain simulations and goniometric measurements," *Applied Optics* 38(16):3651-3661.

Drezek et al. (2000), "Laser Scanning Confocal Microscopy of Cervical Tissue Before and After Application of Acetic Acid," *Am. J. Obstet. Gynecol.*, 182(5):1135-1139.

Dumontier et al. (1999), "Real-time DSP implementation for MRF-based video motion detection," *IEEE Transactions on Image Processing*, 8(10):1341-1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence*, 18(9):927-932.

Edebiri, A.A. (1990), "The relative significance of colposcopic discriptive appearances in the dianosis of cervical intraepithelial neoplasia," *Int. J. Gynecol. Obstet.*, 33:23-29.

Eisner et al. (1987), "Use of Cross-Correlation Function to Detect Patient Motion During Spectral Imaging," *Journal of Nuclear Medicine*, 28(1):97-101.

Ferris et al. (1998), "Colposcopy Quality Control: Establishing Colposcopy Criterion Standards for the NCI ALTS Trial Using Cervigrams," *J. Lower Genital Tract Disease*, 2(4):195-203.

Fleet et al. (1995), "Recursive Filters for Optical Flow," *IEEE Transactions on Pattern Analysis and Machine Intelligence*, 17(1):61-67.

Gao et al. (1998), "A work minimization approach to image morphing," *The Visual Computer*, 14:390-400.

Gauch (1999), "Image Segmentation and Analysis Via Multiscale Gradient Watershed Hierarchies," *IEEE Transactions on Image Processing*, 8(1):69-79.

Hall et al. (1992), "Near-Infrared Spectrophotometry: A New Dimension in Clinical Chemistry", *Clin. Chem.* 38(9):1623-1631.

Haralick (1984), "Digital Step Edges from Zero Crossing of Second Directional Derivatives," *IEEE Transactions on Pattern Analysis and Machine Intelligence*, 6(1):58-68.

Haris et al. (1998), "Hybrid Image Segmentation Using Watersheds and Fast Region Merging," *IEEE Transactions on Image Processing*, 7(12):1684-1699.

Helmerhorst et al. (1987), "The accuracy of colposcopically directed biopsy in diagnosis of CIN ⅔." *Eur. J. Obstet. Gyn. Reprod. Biol.*, 24, 221-229.

Horn et al. (1981), "Determining Optical Flow," *Artificial Intelligence*, 17(1-3):185-203.

Horn et al. (1993), "Determining Optical Flow": a retrospective, *Artificial Intelligence*, 59:81-87.

Huang et al. (1979), "A fast two-dimensional median filtering algorithm," *IEEE Transactions on Acoustics, Speech, and Signal Processing*, 27(1):13-18.

Jackway (1996), "Gradient Watersheds in Morphological Scale-Space," *IEEE Transactions on Image Processing*, 5(6):913-921.

Ji et al. (2000), "Texture Analysis for Classification of Cervix Lesions," *IEEE Transactions on Medical Imaging*, 19(11):1144-1149.

Kierkegaard et al. (1995), "Association between Colposcopic Findings and Histology in Cervical Lesions: The Significance of the Size of the Lesion" *Gynecologic Oncology*, 57:66-71.

Koester (1980), "Scanning Mirror Microscope with Optical Sectioning Characteristics: Applications in Ophthalmology", *Applied Optics*, 19(11):1749-1757.

Koester, "Comparison of Optical Sectioning Methods: The Scanning Slit Confocal Microscope", *Confocal Microscope Handbook*, pp. 189-194.

Kumar et al. (1996), "Optical Flow: A Curve Evolution Approach," *IEEE Transactions on Image Processing*, 5(4):598-610.

Linde et al. (1980), An algorithm for vector quantizer design,: *IEEE Transactions on Communications*, 28(1):84-95.

MacAulay et al. (2002), "Variation of fluorescence spectroscopy during the menstrual cycle," *Optics Express*, 10(12):493-504.

MacLean A.B. (1999), "What is Acetowhite Epithelium," *Abstract Book; 10th World Congress of Cervical Pathology and Colposcopy*, Nov. 7-11, Buenos Aires, Argentina 41.

Marzetta et al. (1999), "A surprising radon transform result and its application to motion detection," *IEEE Transactions on Image Processing*, 8(8):1039-1049.

Miike et al. (1999), "Motion enhancement for preprocessing of optical flow and scientific visualization," *Pattern Recognition Letters*, 20:451-461.

Mikhail et al. (1995), "Computerized colposcopy and conservative management of cervical intraepithelial neoplasia in pregnancy," *Acta Obstet. Gynecol. Scand.*, 74:376-378.

Milanfar (1999), "Two-dimensional matched filtering for motion estimation," *IEEE Transactions on Image Processing*, 8(3):438-444.

Mitchell et al. (1998), "Colposcopy for the diagnosis of squamous intraepithelial lesions: a meta-analysis," *Obstet. Gynecol.*, 91(4):626-631.

Mycek et al. (1998), "Colonic polyp differentiation using time-resolved autofluorescence spectroscopy," *Gastrointestinal Endoscopy*, 48(4):390-394.

Nanda et al. (2000), "Accuracy of the Papanicolaou test in screening for and follow-up of cervical cytologic abnormalities: a systematic review," *Ann Intern Med.*, 132(10):810-819.

Nesi et al. (1998), "RETIMAC REalTIme Motion Analysis Chip," *IEEE Transactions on Circuits and Systems-II: Analog and Digital Signal Processing*, 45(3):361-375.

Noumeir et al. (1996), "Detection of Motion During Tomographic Acquisition by an Optical Flow Algorithm," *Computers and Biomedical Research*, 29(1):1-15.

O'Sullivan et al. (1994), "Interobserver variation in the diagnosis and grading of dyskaryosis in cervical smears: specialist cytopathologists compared with non-specialists," *J. Clin. Pathol.*, 47(6):515-518.

Ogura et al. (1995), "A cost effective motion estimation processor LSI using a simple and efficient algorithm," *IEEE Transactions on Consumer Electronics*, 41(3):690-698.

Okatani et al. (1997), "Shape reconstruction from an endoscope image by shape from shading technique for a point light source at the projection center," *Computer Vision and Image Understanding*, 66(2):119-131.

Pan et al. (1998), "Correlation-feedback Technique in Optical Flow Determination," *IEEE Transactions on Image Processing*, 7(7):1061-1067.

Perona et al. (1990), "Scale-space and edge detection using anisotropic diffusion," *IEEE Transactions on Pattern Analysis and Machine Intelligence*, 12(7):629-639.

Pogue et al. (2001), "Analysis of Acetic Acid-Induced Whitening of High-Grade Squamous Intraepithelial Lesions," *Journal of Biomedical Optics*, 6(4):397-403.

Radjadhyaksha et al. (2000), "Confocal microscopy of excised human skin using acetic acid and crossed polarization: rapid detection of non-melanoma skin cancers," *Proceedings of SPIE*, 3907:84-88.

Rakshit et al. (1997), "Computation of Optical Flow Using Basis Functions," *IEEE Transactions on Image Processing*, 6(9):1246-1254.

Ramanujam et al. (1994) "In vivo diagnosis of cervical intraepithelial neoplasia using 337-nm-exited laser-induced fluorescence", *Pro. Natl. Acad. Sci. USA*, 91:10193-10197.

Ramanujam et al. (1994), "Fluorescence Spectroscopy; A Diagnostic Tool for Cervical Intraepithelial Neoplasia (CIN)," *Gynecologic Oncology*, 52:31-38.

Reid et al. (1985), "Genital warts and cervical cancer. VII. An improved colposcopic index for differentiating benign papillomaviral infections from high-grade CIN," *Am. J. Obstet. Gynecol.*, 153(6):611-618.

Richards-Kortum et al. (1994), "Description and Performance of a Fiber-optic Confocal Fluorescence Spectrometer," *Applied Spectroscopy*, 48(3):350-355.

Romano et al. (1997), "Spectroscopic study of human leukocytes," *Physica Medica*, 13:291-295.

Ruprecht et al. (1995), "Image warping with scattered data interpolation methods," *IEEE Computer Graphics and Applications*, 37-43.

Sakuma (1985), "Quantitative Analysis of the Whiteness of the Atypical Cervical Transformation Zone", *The Journal of Reproductive Medicine*, 30(10):773-776.

Schmid (1999), "Lesion Detection in Dermatoscopic Images Using Anisotropic Diffusion and Morphological Flooding," *Proceedings of the International Conference on Image Processing (ICIP-99)*, 3:449-453.

Schmid (1999), "Segmentation and Symmetry Measure for Image Analysis: Application to Digital Dermatoscopy," *Ph.D. Thesis, Swiss Federal Institute of Technology (EPFL), Signal Processing Laboratory (LTS)*.

Schmid (1999), "Segmentation of Digitized Dermatoscopic Images by 2D Color Clustering," *IEEE Transactions on Medical Imaging*, 18(2):164-171.

Schmitt et al. (1994), "Confocal Microscopy in Turbid Media", *J. Opt. Soc. Am. A*, 11(8):2225-2235.

Schmitt et al. (1994), "Interferometric Versus Confocal Techniques for Imaging Microstructurres in Turbid Biological Media", *Proc. SPIE*, 2135:1-12.

Schomacker et al. (1992), "Ultraviolet Laser-Induced Fluorescence of Colonic Polyps," *Gastroenterology*, 102:1155-1160.

Schomacker et al. (1992), "Ultraviolet Laser-Induced Fluorescence of Colonic Tissue; Basic Biology and Diagnostic Potential", *Lasers in Surgery and Medicine*, 12:63-78.

Schwartz (1993), "Real-time laser-scanning Confocal ratio imaging", *American Laboratory*, pp. 53-62.

Shafarenko et al. (1997), "Automatic Watershed Segmentation of Randomly Textured Color Images," *IEEE Transactions on Image Processing*, 6(11):1530-1544.

Shafi et al. (1995), "Modern Image capture and data collection technology," *Clin. Obstet. Gynecol.*, 38(3):640-643.

Sheppard et al. (1978), "Depth of Field in the Scanning Microscope", *Optics Letters*, 3(3):115-117.

Szarewski et al., (1996), "Effect of smoking cessation on cervical lesions size," *Lancet*, 347:941-943.

Szeliski et al. (1997), "Spline-based image registration," *International Journal of Computer Vision*, 22(3):199-218.

Tadrous (2000), "Methods for Imaging the Structure and Function of Living Tissues and Cells: 2. Fluorescence Lifetime Imaging," *Journal of Pathology*, 191(3):229-234.

Thirion et al. (1999), "Deformation analysis to detect and quantify active lesions in three-dimensional medical image sequences," *IEEE Transactions on Medial Imaging*, 18(5):429-441.

Toglia et al. (1997), "Evaluation of colposcopic skills in an obstetrics and gynecology residency training program," *J. Lower Gen. Tract. Dis.*, 1(1):5-8.

Treameau et al. (1997), "A Region Growing and Merging Algorithm to Color Segmentation," *Pattern Recognition*, 30(7):1191-1203.

Van den Elsen et al. (1995), "Automatic registration of ct and mr brain images using correlation of geometrical features," *IEEE Transactions on medical imaging*, 14(2):384-396.

Vernon (1999), "Computation of Instantaneous Optical Flow Using the Phase of Fourier Components," *Image and Vision Computing*, 17:189-199.

Vincent et al. (1991), "Watersheds in Digital Spaces: An Efficient Algorithm Based on Immersion Simulations," *IEEE Transactions on Patterns Analysis and Machine Intelligence*, 13(6):583-598.

Vincent et al. (1993), "Morphological grayscale reconstruction in image analysis: Applications and efficient algorithms," *IEEE Transactions on Image Processing*, 2(2):176-201.

Wang et al. (1999), "Fast algorithms for the estimation of motion vectors," *IEEE Transactions on Image Processing*, 8(3):435-438.

Weng et al. (1997), "Three-Dimensional Surface Reconstruction Using Optical Flow for Medical Imaging," *IEEE Transactions on Medical Imaging*, 16(5):630-641.

Wilson, "The Role of the Pinhold in Confocal Imaging Systems", *Confocal Microscopy Handbook*, Chapter 11, 113-126.

Wolberg et al. (1998) "Image morphing: a survey," *The Visual Computer*, 14:360-372.

You et al. (1996), "Behavioral analysis of anisotropic diffusion in image processing," *IEEE Transactions on Image Processing*, 5(11):1539-1553.

Zahm et al. (1998), "Colposcopic appearance of cervical intraepithelial neoplasia is age dependent," *Am. J. Obstet. Gynecol.*, 179(5):1298-1304.

Zeger et al. (1992), "Globally optimal vector quantizer design by stochastic relaxation," *IEEE Transactions on Signal Processing*, 40(2):310-322.

Zeng et al. (1993), "A computerized autofluorescence and diffuse reflectance spectroanalyser system for *in vivo* skin studies," *Phys. Med. Biol.*, 38:231-240.

Zeng et al. (1997), "Optimization of fast block motion estimation algorithms," *IEEE Transactions on Circuits and Systems for Video Technology*, 7(6):833-844.

Zhang et al. (1999), "Shape from shading: a survey," *IEEE Transactions on Pattern Analysis and Machine Intelligence*, 21(8):690-706.

Zheng et al. (1991), "Estimation of illumination direction, albedo, and shape from shading," *IEEE Transactions on Pattern Analysis and Machine Intelligence*, 13(7):680-702.

Zhengfang et al. (1998), "Identification of Colonic Dysplasia and Neoplasia by Diffuse Reflectance Spectroscopy and Pattern Recognition Techniques," *Applied Spectroscopy*, 52(6):833-839.

\* cited by examiner

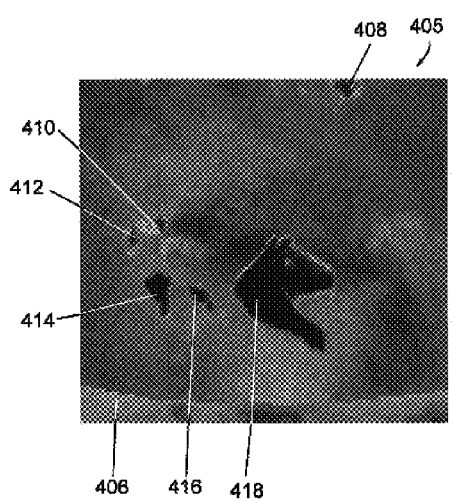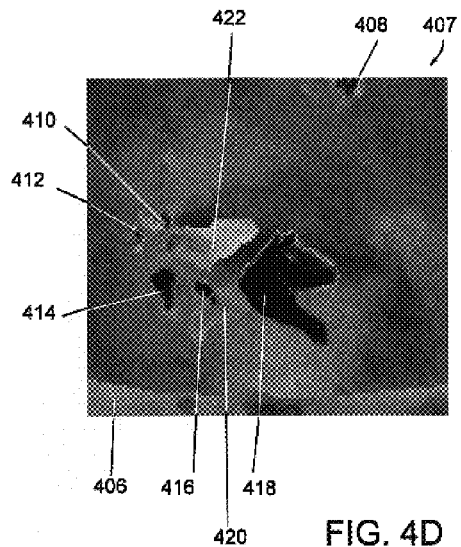
FIG. 4C
FIG. 4D

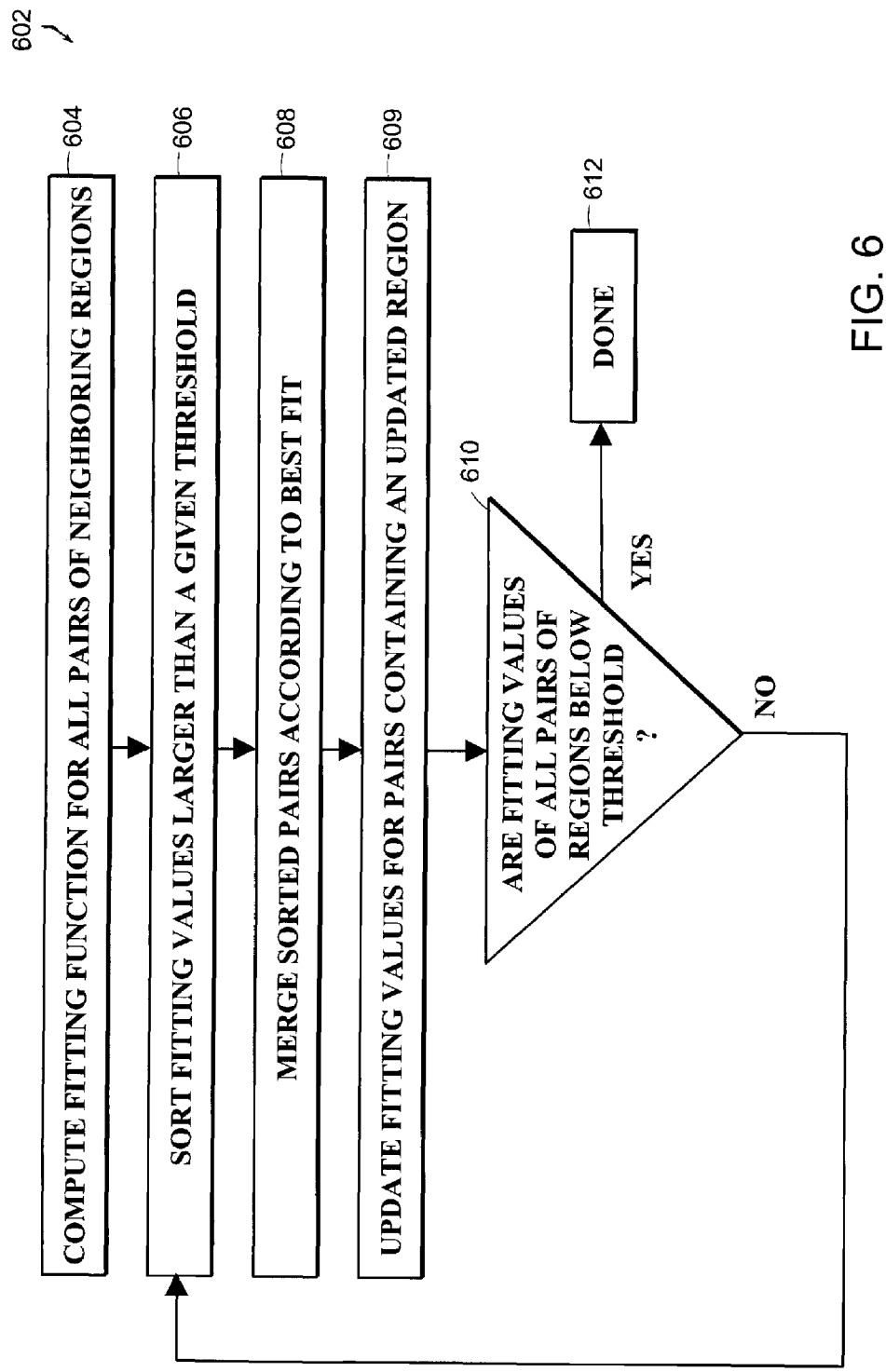

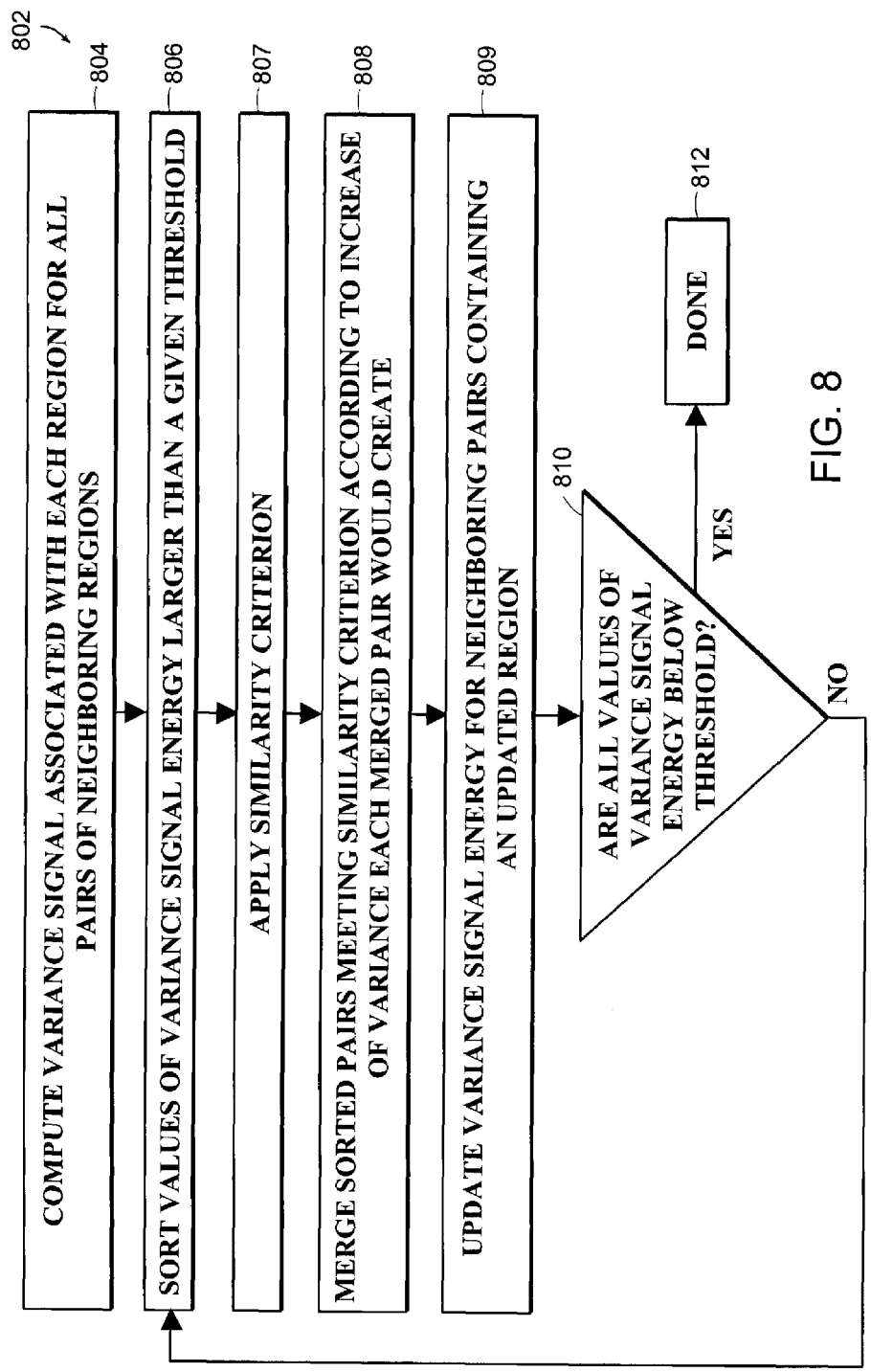

1302

IMAGE PROCESSING USING MEASURES OF SIMILARITY

PRIOR APPLICATIONS

The present application is a continuation-in-part of U.S. patent application Ser. No. 10/068,133, filed Feb. 5, 2002, which is a continuation of U.S. patent application Ser. No. 09/738,614, filed Dec. 15, 2000, which claims priority to and the benefit of U.S. Provisional Patent Application Ser. No. 60/170,972, filed Dec. 15, 1999; also, the present application claims the benefit of U.S. Provisional Patent Application Ser. No. 60/353,978, filed Jan. 31, 2002. All of the above applications are assigned to the common assignee of this application and are hereby incorporated by reference.

GOVERNMENT RIGHTS

This invention was made with government support under Grant No. 1-R44-CA-91618-01 awarded by the U.S. Department of Health and Human Services. The government has certain rights in the invention.

FIELD OF THE INVENTION

This invention relates generally to image processing. More particularly, in certain embodiments, the invention relates to segmentation of a sequence of colposcopic images based on measures of similarity.

BACKGROUND OF THE INVENTION

It is common in the medical field to perform visual examination to diagnose disease. For example, visual examination of the cervix can discern areas where there is a suspicion of pathology. However, direct visual observation alone is often inadequate for identification of abnormalities in a tissue.

In some instances, when tissues of the cervix are examined in vivo, chemical agents such as acetic acid are applied to enhance the differences in appearance between normal and pathological areas. Aceto-whitening techniques may aid a colposcopist in the determination of areas where there is a suspicion of pathology.

However, colposcopic techniques generally require analysis by a highly trained physician. Colposcopic images may contain complex and confusing patterns. In colposcopic techniques such as aceto-whitening, analysis of a still image does not capture the patterns of change in the appearance of tissue following application of a chemical agent. These patterns of change may be complex and difficult to analyze. Current automated image analysis methods do not allow the capture of the dynamic information available in various colposcopic techniques.

Traditional image analysis methods include segmentation of individual images. Segmentation is a morphological technique that splits an image into different regions according to one or more pre-defined criteria. For example, an image may be divided into regions of similar intensity. It may therefore be possible to determine which sections of a single image have an intensity within a given range. If a given range of intensity indicates suspicion of pathology, the segmentation may be used as part of a diagnostic technique to determine which regions of an image may indicate diseased tissue.

However, standard segmentation techniques do not take into account dynamic information, such as a change of intensity over time. This kind of dynamic information is important to consider in various diagnostic techniques such as aceto-whitening colposcopy. A critical factor in discriminating between healthy and diseased tissue may be the manner in which the tissue behaves throughout a diagnostic test, not just at a given time. For example, the rate at which a tissue whitens upon application of a chemical agent may be indicative of disease. Traditional segmentation techniques do not take into account time-dependent behavior, such as rate of whitening.

SUMMARY OF THE INVENTION

The invention provides methods for relating aspects of a plurality of images of a tissue in order to obtain diagnostic information about the tissue. In particular, the invention provides methods for image segmentation across a plurality of images instead of only one image at a time. In a sense, inventive methods enable the compression of a large amount of pertinent information from a sequence of images into a single frame. An important application of methods of the invention is the analysis of a sequence of images of biological tissue in which an agent has been applied to the tissue in order to change its optical properties in a way that is indicative of the physiological state of the tissue. Diagnostic tests which have traditionally required analysis by trained medical personnel may be automatically analyzed using these methods. The invention may be used, for example, in addition to or in place of traditional analysis.

The invention provides methods of performing image segmentation using information from a sequence of images, not just from one image at a time. This is important because it allows the incorporation of time effects in image segmentation. For example, according to an embodiment of the invention, an area depicted in a sequence of images is divided into regions based on a measure of similarity of the changes those regions undergo throughout the sequence. In this way, inventive segmentation methods incorporate more information and can be more helpful, for example, in determining a characteristic of a tissue, than segmentation performed using one image at a time. The phrases "segmentation of an image" and "segmenting an image," as used herein, may apply, for example, to dividing an image into different regions, or dividing into different regions an area in space depicted in one or more images (an image plane).

Segmentation methods of this invention allow, for example, the automated analysis of a sequence of images using complex criteria for determining a disease state which may be difficult or impossible for a human analyst to perceive by simply viewing the sequence. The invention also allows the very development of these kinds of complex criteria for determining a disease state by permitting the relation of complex behaviors of tissue samples during dynamic diagnostic tests to the known disease states of the tissue samples. Criteria may be developed using the inventive methods described herein to analyze sequences of images for dynamic diagnostic tests that are not yet in existence.

One way to relate a plurality of images to each other according to the invention is to create or use a segmentation mask that represents an image plane divided into regions that exhibit similar behavior throughout a test sequence. Another way to relate images is by creating or using graphs or other means of data representation which show mean signal intensities throughout each of a plurality of segmented regions as a function of time. Relating images may also be performed by identifying any particular area represented in an image sequence which satisfies given criteria.

In one aspect, the invention is directed to a method of relating a plurality of images of a tissue. The method includes the steps of: obtaining a plurality of images of a tissue; determining a relationship between two or more regions in each of two or more of the images; segmenting at least a subset of the two or more images based on the relationship; and relating two or more images of the subset of images based at least in part on the segmentation.

According to one embodiment, the step of obtaining a plurality of images of a tissue includes collecting an optical signal. In one embodiment, the optical signal includes fluorescence illumination from the tissue. In one embodiment, the optical signal includes reflectance, or backscatter, illumination from the tissue. In one embodiment, the tissue is illuminated by a white light source, a UV light source, or both. According to one embodiment, the step of obtaining images includes recording visual images of the tissue.

According to one embodiment, the tissue is or includes cervical tissue. In another embodiment, the tissue is one of the group consisting of epithelial tissue, colorectal tissue, skin, and uterine tissue. In one embodiment, the plurality of images being related are sequential images. In one embodiment, the chemical agent is applied to change its optical properties in a way that is indicative of the physiological state of the tissue. According to one embodiment, a chemical agent is applied to the tissue. In one embodiment, the chemical agent is selected from the group consisting of acetic acid, formic acid, propionic acid, butyric acid, Lugol's iodine, Shiller's iodine, methylene blue, toluidine blue, osmotic agents, ionic agents, and indigo carmine. In certain embodiments, the method includes filtering two or more of the images. In one embodiment, the method includes applying either or both of a temporal filter, such as a morphological filter, and a spatial filter, such as a diffusion filter.

In one embodiment, the step of determining a relationship between two or more regions in each of two or more of the images includes determining a measure of similarity between at least two of the two or more images. In one embodiment, determining the measure of similarity includes computing an N-dimensional dot product of the mean signal intensities of two of the two or more regions. In one embodiment, the two regions (of the two or more regions) are neighboring regions.

According to one embodiment, the step of relating images based on the segmentation includes determining a segmentation mask of an image plane, where two or more regions of the image plane are differentiated. In one embodiment, the step of relating images based on the segmentation includes defining one or more data series representing a characteristic of one or more associated segmented regions of the image plane. In one embodiment, this characteristic is mean signal intensity.

According to one embodiment, the step of relating images includes creating or using a segmentation mask that represents an image plane divided into regions that exhibit similar behavior throughout the plurality of images. In one embodiment, the step of relating images includes creating or using graphs or other means of data representation which show mean signal intensities throughout each of a plurality of segmented regions as a function of time. In one embodiment, the step of relating images includes identifying a particular area represented in the image sequence which satisfies given criteria.

In another aspect, the invention is directed to a method of relating a plurality of images of a tissue, where the method includes the steps of: obtaining a plurality of images of a tissue; determining a measure of similarity between two or more regions in each of two or more of the images; and relating at least a subset of the images based at least in part on the measure of similarity. In one embodiment, the step of determining a measure of similarity includes computing an N-dimensional dot product of the mean signal intensities of two of the two or more regions. In one embodiment, the two regions are neighboring regions.

In another aspect, the invention is directed to a method of determining a tissue characteristic. The method includes the steps of: obtaining a plurality of images of a tissue; determining a relationship between two or more regions in each of two or more of the images; segmenting at least a subset of the two or more images based at least in part on the relationship; and determining a characteristic of the tissue based at least in part on the segmentation.

According to one embodiment, the step of obtaining a plurality of images of a tissue includes collecting an optical signal. In one embodiment, the optical signal includes fluorescence illumination from the tissue. In one embodiment, the optical signal includes reflectance, or backscatter, illumination from the tissue. In one embodiment, the tissue is illuminated by a white light source, a UV light source, or both. According to one embodiment, the step of obtaining images includes recording visual images of the tissue.

According to one embodiment, the tissue is or includes cervical tissue. In another embodiment, the tissue is one of the group consisting of epithelial tissue, colorectal tissue, skin, and uterine tissue. In one embodiment, the plurality of images being related are sequential images. In one embodiment, the chemical agent is applied to change its optical properties in a way that is indicative of the physiological state of the tissue. According to one embodiment, a chemical agent is applied to the tissue. In one embodiment, the chemical agent is selected from the group consisting of acetic acid, formic acid, propionic acid, butyric acid, Lugol's iodine, Shiller's iodine, methylene blue, toluidine blue, osmotic agents, ionic agents, and indigo carmine. In certain embodiments, the method includes filtering two or more of the images. In one embodiment, the method includes applying either or both of a temporal filter, such as a morphological filter, and a spatial filter, such as a diffusion filter. In one embodiment, the method includes processing two or more images to compensate for a relative motion between the tissue and a detection device.

According to one embodiment, the step of determining a relationship between two or more regions in each of two or more of the images includes determining a measure of similarity between at least two of the two or more images. In certain embodiments, determining this measure of similarity includes computing an N-dimensional dot product of the mean signal intensities of two of the two or more regions. In one embodiment, the two regions are neighboring regions.

According to one embodiment, the segmenting step includes analyzing an aceto-whitening signal. In one embodiment, the segmenting step includes analyzing a variance signal. In one embodiment, the segmenting step includes determining a gradient image.

According to one embodiment, the method includes processing one or more optical signals based on the segmentation. In one embodiment, the method includes filtering at least one image based at least in part on the segmentation.

In certain embodiments, the step of determining a characteristic of the tissue includes determining one or more regions of the tissue where there is suspicion of pathology. In certain embodiments, the step of determining a characteristic of the tissue includes classifying a region of tissue as one of the following: normal squamous tissue, metaplasia, Cervical Intraepithelial Neoplasia, Grade I (CIN I), and Cervical Intraepithelial Neoplasia, Grade II or Grade III (CIN II/CIN III).

In another aspect, the invention is directed to a method of determining a characteristic of a tissue. The method includes the steps of: (a) for each of a first plurality of reference sequences of images of tissue having a first known characteristic, quantifying one or more features of each of a first plurality of mean signal intensity data series corresponding to segmented regions represented in each of the first plurality of reference sequences of images; (b) for a test sequence of images, quantifying one of more features of each of one or more mean signal intensity data series corresponding to one or more segmented regions represented in the test sequence of images; and (c) determining a characteristic of a tissue represented in the test sequence of images based at least in part on a comparison between the one or more features quantified in step (a) and the one or more features quantified in step (b).

According to one embodiment, step (c) includes repeating step (a) for each of a second plurality of reference sequences of images of tissue having a second known characteristic. In one embodiment, step (c) includes applying a classification rule based at least in part on the first plurality of reference sequences and the second plurality of reference sequences. In one embodiment, step (c) includes performing a linear discriminant analysis to determine the classification rule. In one embodiment, one of the one or more features of step (a) includes the slope of a curve at a given point fitted to one of the plurality of mean signal intensity data series. According to one embodiment, the method includes determining the segmented regions of the test sequence of images by analyzing an acetowhitening signal. In one embodiment, the first known characteristic is CIN II/CIN III and the second known characteristic is absence of CIN II/CIN III.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

The patent or application file contains at least one drawing executed in color. Copies of this patent or patent application publication with color drawing(s) will be provided by the U.S. Patent and Trademark Office upon request and payment of the necessary fee.

FIGS. 2A and 2A-1 depict human cervix tissue and show an area of which a sequence of images are to be obtained according to an illustrative embodiment of the invention.

FIG. 4C depicts the image representation of FIG. 4B after accounting for glare, used in preprocessing a sequence of images of tissue according to an illustrative embodiment of the invention.

FIG. 4D depicts the image representation of FIG. 4C after accounting for chromatic artifacts, used in preprocessing a sequence of images of tissue according to an illustrative embodiment of the invention.

FIG. 6 is a schematic flow diagram depicting a region merging approach of segmentation according to an illustrative embodiment of the invention.

FIG. 8 is a schematic flow diagram depicting a robust region merging approach of segmentation according to an illustrative embodiment of the invention.

DESCRIPTION OF THE ILLUSTRATIVE EMBODIMENT

In general, the invention provides methods for image segmentation across a plurality of images. Segmentation across a plurality of images provides a much more robust analysis than segmentation in a single image. Segmentation across multiple images according to the invention allows incorporation of a temporal element (e.g., the change of tissue over time in a sequence of images) in optics-based disease diagnosis. The invention provides means to analyze changes in tissue over time in response to a treatment. It also provides the ability to increase the resolution of segmented imaging by increasing the number of images over time. This allows an additional dimension to image-based tissue analysis, which leads to increase sensitivity and specificity of analysis. The following is a detailed description of a preferred embodiment of the invention.

Figure 1:
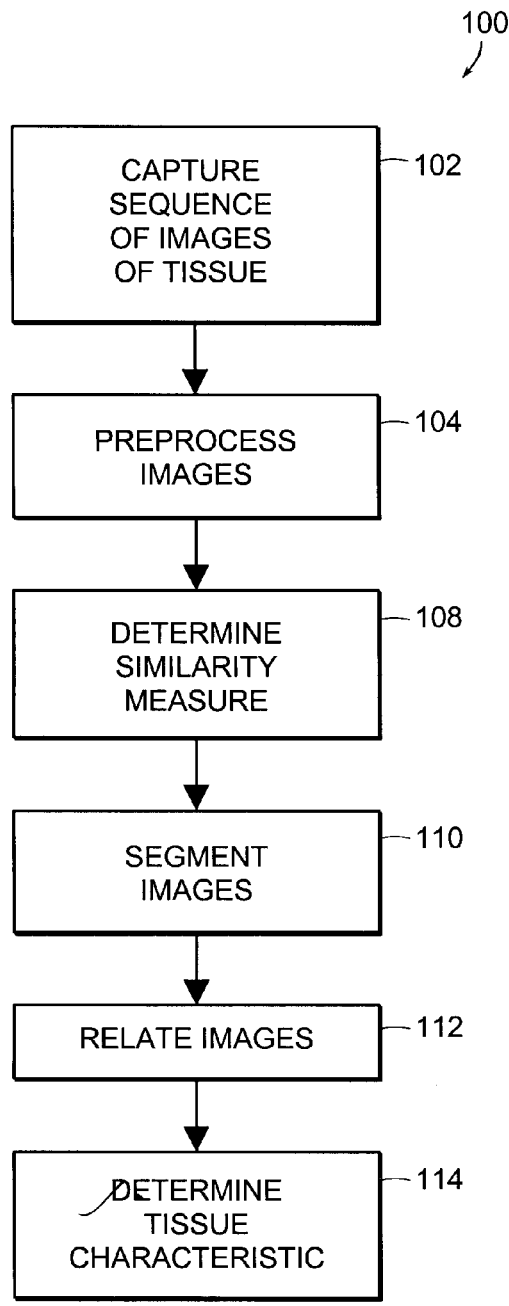
FIG. 1 is a schematic flow diagram depicting steps in the analysis of a sequence of images of tissue according to an illustrative embodiment of the invention.

The schematic flow diagram 100 of FIG. 1 depicts steps in the analysis of a sequence of images of tissue according to an illustrative embodiment of the invention. FIG. 1 also serves as a general outline of the contents of this description. Each of the steps of FIG. 1 is discussed herein in detail. Briefly, the steps include obtaining a sequence of images of the tissue 102, preprocessing the images 104, determining a measure of similarity between regions in each of the images 108, segmenting the images 110, relating the images 112, and finally, determining a tissue characteristic 114. Though not pictured in FIG. 1, the steps may be preceded by application of a chemical agent onto the tissue, for example. In other embodiments, a chemical agent is applied during the performance of the steps of the schematic flow diagram 100 FIG. 1.

Among the key steps of the inventive embodiments discussed here are determining a measure of similarity between regions of tissue represented in a sequence of images and segmenting the images based on the measure of similarity. Much of the mathematical complexity presented in this description regards various methods of performing these key steps. As will become evident, different segmentation methods have different advantages. The segmentation techniques of the inventive embodiments discussed herein include region merging, robust region merging, clustering, watershed, and region growing techniques, as well as combinations of these techniques.

Figure 2A:
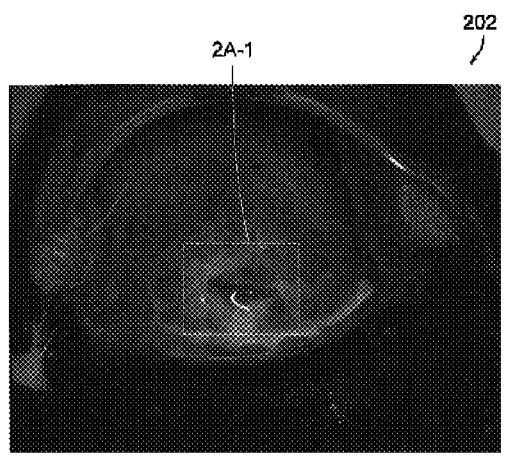
Figures 1, 2A:
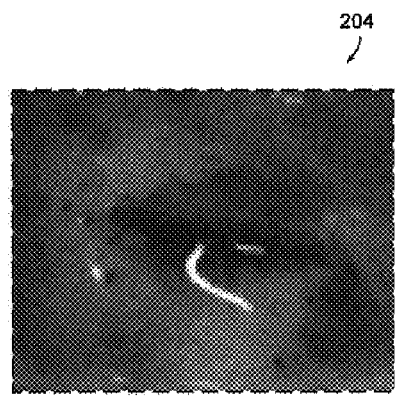
Figure 2B:
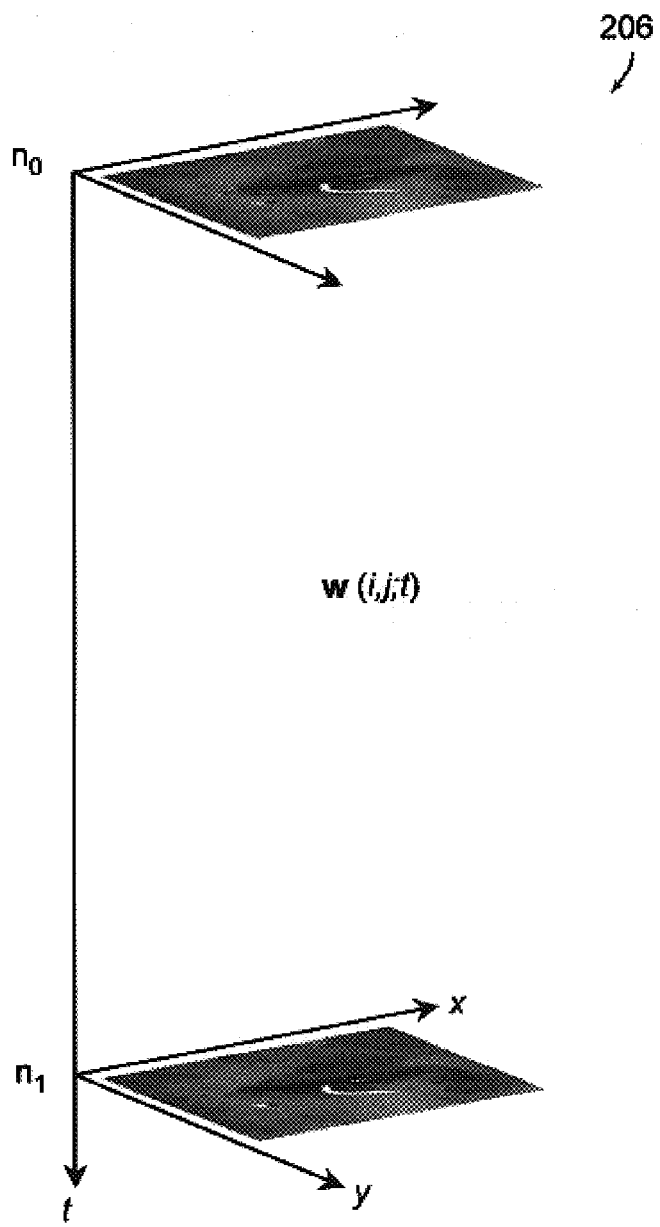
FIG. 2B depicts the characterization of a discrete signal from a sequence of images of tissue according to an illustrative embodiment of the invention.

FIGS. 2A, 2A-1, and 2B relate to step 102 of FIG. 1, obtaining a sequence of images of the tissue. Although embodiments of the invention are not limited to acetowhitening tests, an exemplary sequence of images from an aceto-whitening test performed on a patient is used herein to illustrate certain embodiments of the invention. FIG. 2A depicts a full-frame image 202 of a human cervix after application of acetic acid, at the start of an aceto-whitening test. The inset image 204 depicts an area of interest to be analyzed herein using embodiment methods of the invention. This area of interest may be determined by a technician or may be determined in a semi-automated fashion using a multi-step segmentation approach such as one of those discussed herein below.

FIG. 2B depicts the characterization 206 of a discrete signal $w(i,j;t)$ from a sequence of images of tissue according to an illustrative embodiment of the invention. The signal could be any type of image signal of interest known in the art. In the illustrative embodiment, the signal is an intensity signal of an image.

In the illustrative embodiment, images of an area of interest are taken at N time steps $\{t_0, t_1, \ldots, t_{N-1}\}$. In one embodiment, time $t_0$ corresponds to the moment of application of a chemical agent to the tissue, for instance, and time $t_{N-1}$ corresponds to the end of the test. In another embodiment, time $t_0$ corresponds to a moment following the application of a chemical agent to the tissue. For example, let $\mathbb{I}=\{0, \ldots, r-1\} \times \{0, \ldots, c-1\}$ and $\mathbb{T}=\{n_0, \ldots, n_{N-1}\}$ be the image and time domains, respectively, where r is the number of rows and c is the number of columns. Then, r×c discrete signals w(i,j;t) may be constructed describing the evolution of some optically-detectable phenomena, such as aceto-whitening, with time. For an aceto-whitening example, the "whiteness" may be computed from RGB data of the images. There are any number of metrics which may be used to define "whiteness." For instance, an illustrative embodiment employs an intensity component, CCIR 601, as a measure of "whiteness" of any particular pixel, defined in terms of red (R), green (G), and blue (B) intensities as follows:

$$I = 0.299R + 0.587G + 0.114B. \quad (1)$$

The "whitening" data is then given by w(i,j;t)=I(i,j;n), for example. Alternatively, the signal w(i,j;t) is defined in any of a multiplicity of other ways. The characterization 206 of FIG. 2B shows that the intensity signal w(i,j;t) has a value corresponding to each discrete location (i,j) in each of the images taken at N discrete time steps. According to the illustrative embodiment, a location (i,j) in an image corresponds to a single pixel. In an aceto-whitening example, since it is the whitening of the cervix that is of interest and not the absolute intensity of the cervix surface, the whitening signals are background subtracted. In one example of background subtraction, each of the signals corresponding to a given location at a particular time step are transformed by subtracting the initial intensity signal at that location as shown in Equation (2):

$$w(i,j;n) \mapsto w(i,j;n) - w(i,j;n_0), \forall n \in \mathbb{T}. \quad (2)$$

Noise, glare, and sometimes chromatic artifacts may corrupt images in a sequence. Signal noise due to misaligned image pairs and local deformations of the tissue may be taken into account as well. Alignment functions and image restoration techniques often do not adequately reduce this type of noise. Therefore, it may be necessary to apply temporal and spatial filters.

Figure 3A:
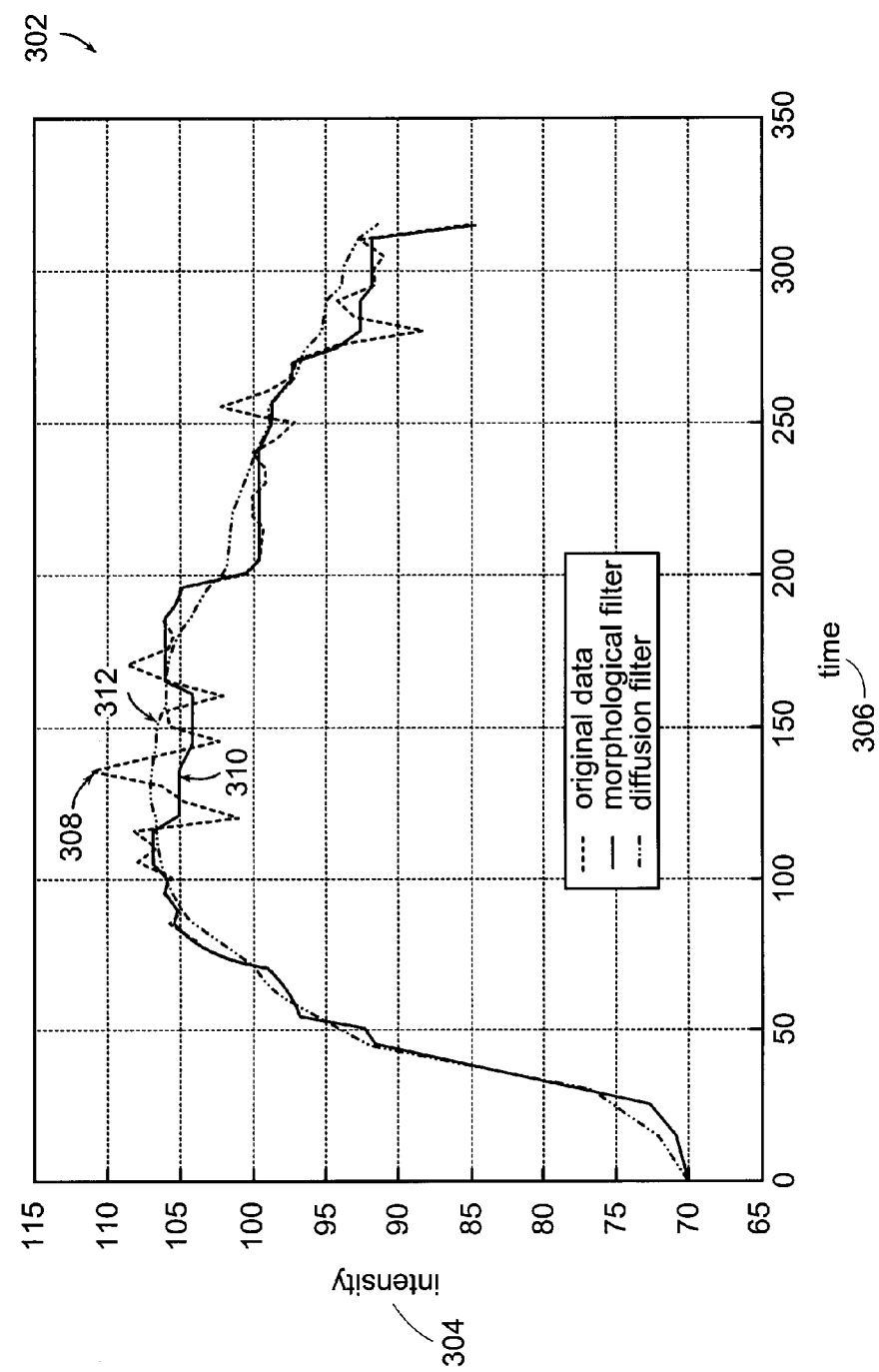
FIGS. 3A and 3B show a series of graphs depicting mean signal intensity of a region as a function of time, as determined from a sequence of images according to an illustrative embodiment of the invention.
Figure 3B:
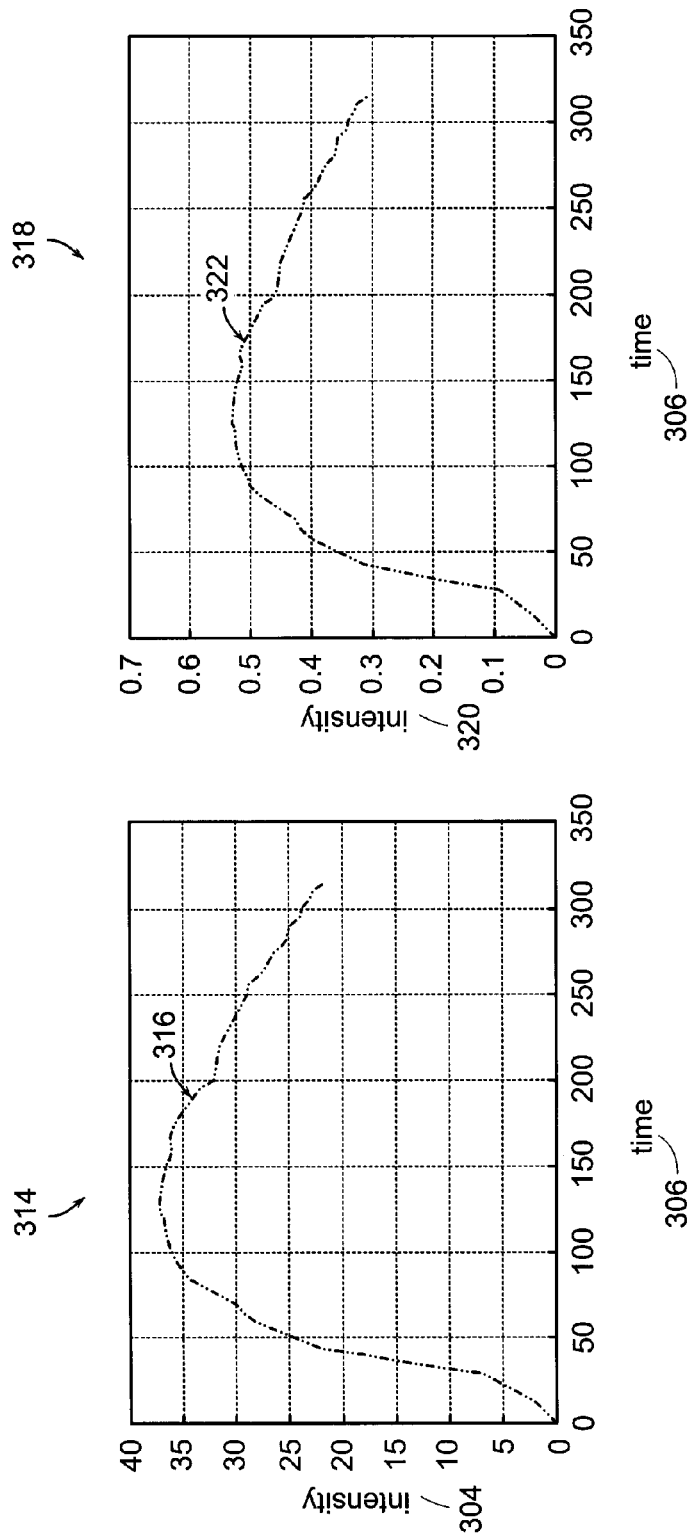

FIGS. 3A and 3B relate to part of step 104 of FIG. 1, preprocessing the images. FIGS. 3A and 3B show a series of graphs depicting mean signal intensity 304 of a pixel as a function of time 306, as determined from a sequence of images according to an illustrative embodiment of the invention. The graphs depict application of a morphological filter, application of a diffusion filter, modification of intensity data to account for background intensity, and normalization of intensity data, according to an illustrative embodiment of the invention.

According to the illustrative embodiment, a first filter is applied to the time axis, individually for each pixel. The images are then spatially filtered. Graph 302 of FIG. 3A depicts the application of both a temporal filter and a spatial filter at a representative pixel. The original data is connected by a series of line segments 308. It is evident from graph 302 that noise makes the signal choppy and adversely affects further analysis if not removed.

For temporal filtering, the illustrative embodiment of the invention applies the morphological filter of Equation (3):

$$w(t) \odot b = \tfrac{1}{2}[(w \circ b) \bullet b + (w \bullet b) \circ b], \quad (3)$$

where b is the structuring element, $\circ$ is the opening operator, and $\bullet$ is the closing operator. According to the illustrative embodiment, the structuring element has a half circle shape. The temporally-filtered data is connected by a series of line segments 310 in the graph 302 of FIG. 3A. The noise is decreased from the series 308 to the series 310.

Illustratively, the images are then spatially filtered, for example, with either an isotropic or a Gaussian filter. A diffusion equation implemented by an illustrative isotropic filter may be expressed as Equation (4):

$$\frac{\partial w(i,j)}{\partial \tau} k \nabla \cdot \nabla w = k \nabla w, \quad (4)$$

where $\nabla$ is the gradient operator, $\Delta$ is the Laplacian operator, and $\tau$ is the diffusion time (distinguished from the time component of the whitening signal itself). An isotropic filter is iterative, while a Gaussian filter is an infinite impulse response (IIR) filter. The iterative filter of Equation (4) is much faster than a Gaussian filter, since the iterative filter allows for increasing smoothness by performing successive iterations. The Gaussian filter requires re-applying a more complex filter to the original image for increasing degrees of filtration. According to the illustrative embodiment, the methods of the invention perform two iterations. However, in other embodiments, the method performs one iteration or three or more iterations. The spatially-filtered data for a representative pixel is connected by a series of line segments 312 in graph 302 of FIG. 3A. The noise is decreased from series 310 to series 312.

Graph 314 of FIG. 3B shows the application of Equation (2), background subtracting the intensity signal 304. Graph 318 of FIG. 3B shows the intensity signal data following normalization 320. In the illustrative embodiment, as explained below in further detail, normalization includes division of values of the intensity signal 304 by a reference value, such as the maximum intensity signal over the sequence of images. Glare and chromatic artifacts can affect selection of the maximum intensity signal; thus, in an illustrative embodiment, normalization is performed subsequent to correcting for glare and chromatic artifacts.

In the illustrative embodiment, the invention masks glare and chromatic artifacts from images prior to normalization. In the case of whitening data, glare may have a negative impact, since glare is visually similar to the tissue whitening that is the object of the analysis. Chromatic artifacts may have a more limited impact on the intensity of pixels and may be removed with the temporal and spatial filters described above.

Thresholding may be used to mask out glare and chromatic artifacts. In the illustrative embodiment thresholding is performed in the L*u*v* color space. Preferably, the invention also employs a correlate for hue, expressed as in Equation (5):

$$h^* = a\tan\left(\frac{v^*}{u^*}\right) \quad (5)$$

Since the hue $h^*$ is a periodic function, the illustrative methods of the invention rotate the u*-v* plane such that the typical reddish color of the cervix correlates to higher values of h*. This makes it possible to work with a single threshold for chromatic artifacts. The rotation is given by Equation (6):

$$\begin{pmatrix} u^* \\ v^* \end{pmatrix} \mapsto \begin{pmatrix} \cos(-\frac{\pi}{3}) & \sin(\frac{\pi}{3}) \\ -\sin(\frac{\pi}{3}) & \cos(\frac{\pi}{3}) \end{pmatrix} \begin{pmatrix} u^* \\ v^* \end{pmatrix}. \quad (6)$$

The masks for glare and chromatic artifacts are then respectively obtained using Equations (7) and (8):

$$\text{mask}_{glare} = L^* > 90 \quad (7)$$

$$\text{mask}_{hue} = h^* < \pi/5, \quad (8)$$

where $L^* \epsilon [0,100]$ and $h^* \epsilon [0,2\pi]$. According to the illustrative embodiment, the masks are eroded to create a safety margin, such that they are slightly larger than the corrupted areas.

Figure 4A:
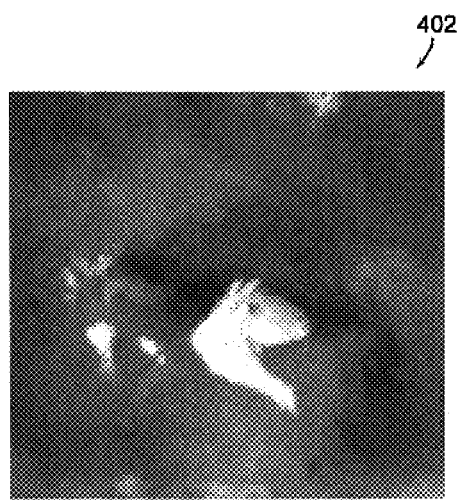
FIG. 4A depicts a "maximum" RGB image representation used in preprocessing a sequence of images of tissue according to an illustrative embodiment of the invention.
Figure 4B:
FIG. 4B depicts the image representation of FIG. 4A after applying a manual mask, used in preprocessing a sequence of images of tissue according to an illustrative embodiment of the invention.

FIGS. 4A and 4B relate to part of step 104 of FIG. 1, preprocessing the images. FIG. 4A depicts a "maximum" RGB image representation 402 used in preprocessing a sequence of images of tissue according to an illustrative embodiment of the invention. In the illustrative embodiment, the maximum RGB image is computed by taking for each pixel the maximum RGB values in the whole sequence of images.

FIG. 4B depicts the image representation of FIG. 4A after applying a manual mask, used in preprocessing a sequence of images of tissue according to an illustrative embodiment of the invention. According to the illustrative embodiment, the method applies the manual mask in addition to the masks for glare and chromatic effects in order to account for obstructions such as hair, foam from the chemical agent, or other obstruction, and/or to narrow analysis to an area of interest. Area 406 of the frame 404 of FIG. 4B has been manually masked in accord with the methods of the embodiment.

FIG. 4C, which depicts the image representation of FIG. 4B after accounting for glare, is used in preprocessing a sequence of images of tissue according to an illustrative embodiment of the invention. Note that the areas 408, 410, 412, 414, 416, and 418 of the frame 405 of FIG. 4C have been masked for glare using Equation (7).

FIG. 4D, which depicts the image representation of FIG. 4C after accounting for chromatic artifacts, is used in preprocessing a sequence of images of tissue according to an illustrative embodiment of the invention. The areas 420 and 422 of the frame 407 of FIG. 4D have been masked for chromatic artifacts using Equation (8).

To reduce the amount of data to process and to improve the signal-to-noise ratio of the signals used in the segmentation techniques discussed below, illustrative methods of the invention pre-segment the image plane into grains. Illustratively, the mean grain surface is about 30 pixels. However, in other embodiments, it is between about a few pixels and about a few hundred pixels. The segmentation methods can be applied starting at either the pixel level or the grain level.

One way to "pre-segment" the image plane into grains is to segment each of the images in the sequence using a watershed transform. One goal of the watershed technique is to simplify a gray-level image by viewing it as a three-dimensional surface and by progressively "flooding" the surface from below through "holes" in the surface. In one embodiment, the third dimension is the gradient of an intensity signal over the image plane (further discussed herein below). A "hole" is located at each minimum of the surface, and areas are progressively flooded as the "water level" reaches each minimum. The flooded minima are called catchment basins, and the borders between neighboring catchment basins are called watersheds. The catchment basins determine the pre-segmented image.

Image segmentation with the watershed transform is preferably performed on the image gradient. If the watershed transform is performed on the image itself, and not the gradient, the watershed transform may obliterate important distinctions in the images. Determination of a gradient image is discussed herein below.

Segmentation is a process by which an image is split into different regions according to one or more pre-defined criteria. In certain embodiments of the invention, segmentation methods are performed using information from an entire sequence of images, not just from one image at a time. The area depicted in the sequence of images is split into regions based on a measure of similarity of the detected changes those regions undergo throughout the sequence.

Segmentation is useful in the analysis of a sequence of images such as in aceto-whitening cervical testing. In an illustrative embodiment, since the analysis of time-series data with a one-pixel resolution is not possible unless motion, artifacts, and noise are absent or can be precisely identified, segmentation is needed. Often, filtering and masking procedures are insufficient to adequately relate regions of an image based on the similarity of the signals those regions produce over a sequence of images. Therefore, the illustrative methods of the invention average time-series data over regions made up of pixels whose signals display similar behavior over time.

In the illustrative embodiment, regions of an image are segmented based at least in part upon a measure of similarity of the detected changes those regions undergo. Since a measure of similarity between regions depends on the way regions are defined, and since regions are defined based upon criteria involving the measure of similarity, the illustrative embodiment of the invention employs an iterative process for segmentation of an area into regions. In some embodiments, segmentation begins by assuming each pixel or each grain (as determined above) represents a region. These individual pixels or grains are then grouped into regions according to criteria defined by the segmentation method. These regions are then merged together to form new, larger regions, again according to criteria defined by the segmentation method.

A problem that arises when processing raw image data is its high dimension. With a typical whitening signal for a single pixel described by, for example, a sixty-or-more-dimensional vector, it is often necessary to reduce data dimensionality prior to processing. In the illustrative embodiment, the invention obtains a scalar that quantifies a leading characteristic of two vectors. More particularly, illustrative methods of the invention take the N-dimensional inner (dot) product of two vectors corresponding to two pixel coordinates. A fitting function based on this dot product is shown in Equation (9). This fitting function quantifies the similarity between the signals at two locations.

$$\varphi(x_1, x_2) = \frac{\langle w(x_1;t), w(x_2;t) \rangle}{\max(\Omega(x_1), \Omega(x_2))}, \quad (9)$$

where $x_1$ and $x_2$ are two pixel coordinates, and $\Omega(x_1) = \langle w(x_1;t), w(x_1;t) \rangle$ is the energy of the signal at location $x_1$.

Figure 5:
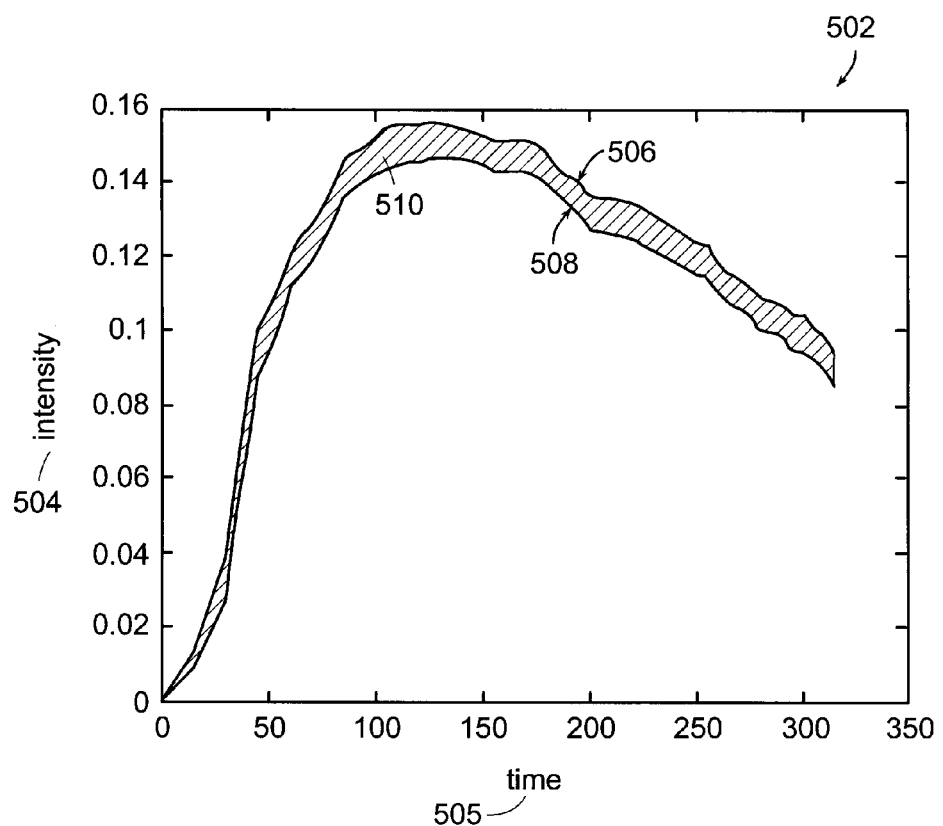
FIG. 5 shows a graph illustrating the determination of a measure of similarity of time series of mean signal intensity for each of two regions according to an illustrative embodiment of the invention.

FIG. 5 relates to step 108 of FIG. 1, determining a measure of similarity between regions in each of a series of images. FIG. 5 shows a graph 502 illustrating the determination of a measure of similarity of a time series of mean signal intensity 504 for each of two regions k and l according to an illustrative embodiment of the invention. FIG. 5 represents one step in an illustrative segmentation method in which the similarity between the time-series signals of two neighboring regions is compared against criteria to determine whether those regions should be merged together. The type of measure of similarity chosen may vary depending on the segmentation method employed.

Curve 506 in FIG. 5 represents the mean signal intensity 504 of region k in each of a sequence of images and is graphed versus time 505. Mean signal intensity 504 of region k is expressed as in Equation (10):

$$w(k;t) = \frac{1}{N_k} \sum_{(i,j) \in S_k} w(i,j;t), \quad (10)$$

where $S_k \subset \mathbb{N}^2$ is the set of all pixels that belong to the $k^{th}$ region and $N_k$ is the size of $S_k$.

Curve 508 of FIG. 5 represents the mean signal intensity 504 of region l and is graphed versus time 505. Mean signal intensity 504 of region l is expressed as in Equation (10), replacing "k" with "l" in appropriate locations. The shaded area 510 of FIG. 5 represents dissimilarity between mean signals over region k and region l. The chosen measure of similarity, $\phi_{kl}$, also referred to herein as the fitting function, between regions k and l may depend on the segmentation method employed. For the region merging segmentation technique, discussed in more detail below, as well as for other segmentation techniques, the measure of similarity used is shown in Equation (11):

$$\varphi_{kl} = \frac{\langle w(k;t), w(l;t) \rangle}{\max(\Omega(k), \Omega(l))}, \quad (11)$$

where the numerator represents the N-dimensional dot product of the background-subtracted mean signal intensities 504 of region k and region l; the denominator represents the greater of the energies of the signals corresponding to regions k and l, $\Omega(k)$ and $\Omega(l)$; and $-1 \leq \phi_{kl} \leq 1$. In this embodiment, the numerator of Equation (11) is normalized by the higher signal energy and not by the square root of the product of both energies.

In the case of whitening signals, for example, the fitting function defined by Equation (9) can be used to obtain a gradient image representing the variation of whitening values in x-y space. The gradient of an image made up of intensity signals is the approximation of the amplitude of the local gradient of signal intensity at every pixel location. The watershed transform is then applied to the gradient image. This may be done when pre-segmenting images into "grains" as discussed above, as well as when performing the hierarchical watershed segmentation approach and combined method segmentation approaches discussed below.

A gradient image representing a sequence of images is calculated for an individual image by computing the fitting value $\phi(i,j;i_o,j_o)$ between a pixel $(i_o, j_o)$ and all its neighbors $(i,j) \in \mathbb{N}_{(i_o,j_o)}$, where $\mathbb{N}_{(i_o,j_o)} = \{(i_0-1,j_0),(i_0,j_0-1),(i_0+1,j_0),(i_0,j_0+1)\}$.

Since the best fit corresponds to a null gradient, the derivative of the fitting value is computed as in Equation (12):

$$\varphi_\nabla(i, j; i_0, j_0) = \delta 1 - \frac{\varphi(i, j; i_0, j_0)}{1 + \varphi(i, j; i_0, j_0)}, \quad (12)$$

where $\varphi_\nabla(i, j; i_0, j_0) \in (-\infty, \infty)$. (13)

The sign of $\varphi_\nabla(i, j; i_0, j_0)$ is given by Equation (13):

$$\delta = \begin{cases} 1 & \text{if } \Omega(i_0, j_0) \geq \Omega(i, j) \\ -1 & \text{if } \Omega(i_0, j_0) < \Omega(i, j) \end{cases}.$$

Then, the derivatives of the signals are approximated as the mean of the forward and backward differences shown in Equations (14) and (15).

$$\frac{d}{dx}w(i_0, j_0) = \frac{\varphi_\nabla(i_0, j_0-1; i_0, j_0) - \varphi_\nabla(i_0, j_0+1; i_0, j_0)}{2} \quad (14)$$

$$\frac{d}{dy}w(i_0, j_0) = \frac{\varphi_\nabla(i_0-1, j_0; i_0, j_0) - \varphi_\nabla(i_0+1, j_0; i_0, j_0)}{2}. \quad (15)$$

The norm of the gradient vector is then calculated from the approximations of Equations (14) and (15).

Since the fitting values include information from the entire sequence of images, one may obtain a gradient image which includes information from the entire sequence of images, and which, therefore, shows details not visible in all of the images. The gradient image may be used in the watershed pre-segmentation technique discussed herein above and the hierarchical watershed technique discussed herein below. Had the gradient image been obtained from a single reference image, less detail would be included, and the application of a watershed segmentation method to the gradient image would segment the image plane based on less data. However, by using a gradient image as determined from Equations (14) and (15), the invention enables a watershed segmentation technique to be applied which divides an image plane into regions based on an entire sequence of data, not just a single reference image.

FIG. 6 relates to step 110 of FIG. 1, segmenting the area represented in a sequence of images into regions based on measures of similarity between regions over the sequence. Various techniques may be used to perform the segmentation step 110 of FIG. 1. FIG. 6 shows a schematic flow diagram 602 depicting a region merging technique of segmentation according to an illustrative embodiment of the invention. In this technique, each grain or pixel is initially a region, and the method merges neighboring according to a predefined criterion in an iterative fashion. The criterion is based on a measure of similarity, also called a fitting function. The segmentation converges to the final result when no pair of neighboring regions satisfies the merging criterion. In the case of aceto-whitening data, for instance, it is desired to merge regions whose whitening data is similar. The fitting function will therefore quantify the similarity over the sequence between two signals corresponding to two neighboring regions.

Thus, the segmentation begins at step 604 of FIG. 6, computing the fitting function to obtain "fitting values" for all pairs of neighboring regions. In the region merging approach, this is the measure of similarity provided by Equation (11), where mean signal intensity of a region k is defined by Equation (10). This fitting function is equivalent to the minimum normalized Euclidean distance, $\delta^2_{kl}$, between the mean signal intensities of regions k and l shown in Equation (16):

$$\delta^2_{kl} = \frac{\|w(k;t) - w(l;t)\|^2_{L_2}}{\max(\Omega(k), \Omega(l))} \qquad (16)$$

$$= 2\left(\frac{1}{2}\left(1 + \frac{\min(\Omega(k), \Omega(l))}{\max(\Omega(k), \Omega(l))}\right) - \frac{\langle w(k;t), w(l;t)\rangle}{\max(\Omega(k), \Omega(l))}\right).$$

This notation reveals the effect of normalizing using the higher energy of the two signals instead of normalizing each signal by its $L_2$ norm. The method using Equation (16) or Equation (11) applies an additional "penalty" when both signals have different energies, and therefore, fitting values are below 1.0 when the scaled versions of the two signals are the same, but their absolute values are different.

In step 606 of FIG. 6, the fitting values (measures of similarity) corresponding to pairs of neighboring regions that are larger than a given threshold are sorted from greatest to least. In step 608, sorted pairs are merged according to best fit, keeping in mind that each region can only be merged once during one iteration. For instance, if neighboring regions k and l have a fitting value of 0.80 and neighboring regions k and m have a fitting value of 0.79, regions k and l are merged together, not k and m. However, region m may be merged with another of its neighboring regions during this iteration, depending on the fitting values computed.

In step 609, the method recalculates fitting values for all pairs of neighboring regions containing an updated (newly merged) region. In the embodiment, Fitting values are not recalculated for pairs of neighboring regions whose regions are unchanged.

In step 610 of FIG. 6, it is determined whether the fitting values of all pairs of neighboring regions are below a given threshold. The fitting function is a measure of similarity between regions; thus, the higher the threshold, the more similar regions have to be in order to be merged, resulting in fewer iterations and, therefore, more regions that are ultimately defined. If the fitting values of all the regions are below the given threshold, the merging is complete 612. If not, the process beginning at step 606 repeats, and fitting values of the pairs of neighboring regions as newly defined are sorted.

Once merging is complete 612, a size rule is applied that forces each region whose size is below a given value to be merged with its best fitting neighboring region, even though the fitting value is lower than the threshold. In this way, very small regions not larger than a few pixels are avoided.

The segmentation method of FIG. 6, or any of the other segmentation methods discussed herein, is performed, for example, where each pixel has up to four neighbors: above, below, left, and right. However, in other illustrative embodiments, segmentation is performed where each pixel can has up to eight neighbors or more, which includes diagonal pixels. It should also be noted that images in a given sequence may be sub-sampled to reduce computation time. For instance, a sequence of 100 images may be reduced to 50 images by eliminating every other image from the sequence to be segmented.

Figure 7A:
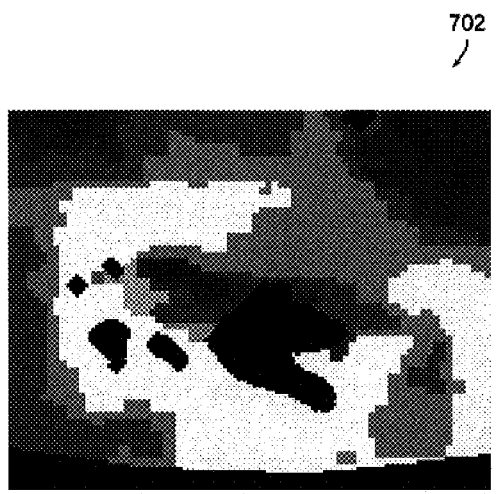
FIG. 7A represents a segmentation mask produced using a region merging approach according to an illustrative embodiment of the invention.
Figure 7B:
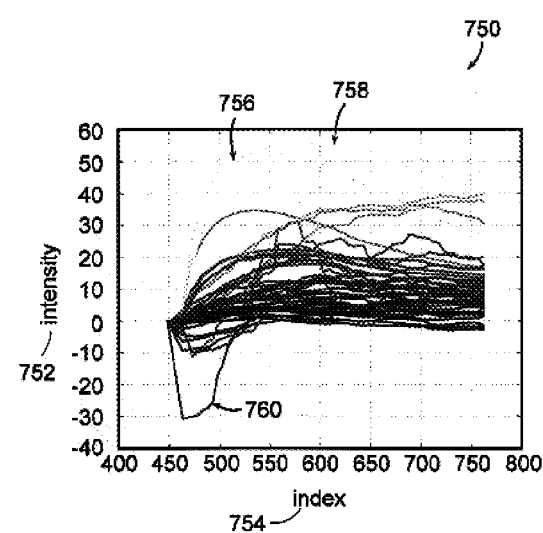
FIG. 7B shows a graph depicting mean signal intensities of segmented regions represented in FIG. 7A as functions of time according to an illustrative embodiment of the invention.

FIGS. 7A and 7B illustrate step 112 of FIG. 1, relating images after segmentation. FIG. 7A depicts a segmentation mask 702 produced using the region merging segmentation technique discussed above for an exemplary aceto-whitening sequence. In an illustrative embodiment, the threshold used in step 610 of FIG. 6 to produce this segmentation mask 702 is 0.7. Each region has a different label, and is represented by a different color in the mask 702 in order to improve the contrast between neighboring regions. Other illustrative embodiments use other kinds of display techniques known in the art, in order to relate images of the sequence based on segmentation and/or based on the measure of similarity.

FIG. 7B shows a graph 750 depicting mean signal intensities 752 of segmented regions represented in FIG. 7A as functions of a time index 754 according to an illustrative embodiment of the invention. The color of each data series in FIG. 7B corresponds to the same-colored segment depicted in FIG. 7A. This is one way to visually relate a sequence of images using the results of segmentation. For instance, according to the illustrative embodiment, regions having a high initial rate of increase of signal intensity 752 are identified by observing data series 756 and 758 in FIG. 7B, whose signal intensities 752 increase more quickly than the other data series. The location of the two regions corresponding to these two data series is found in FIG. 7A. In another example, kinetic rate constants are derived from each of the data series determined in FIG. 7B, and the regions having data series most closely matching kinetic rate constants of interest are identified. In another example, one or more data series are curve fit to obtain a characterization of the mean signal intensities 752 of each data series as functions of time.

Mean signal intensity may have a negative value after background subtraction. This is evident, for example, in the first part of data series 760 of FIG. 7B. In some examples, this is due to the choice of the reference frame for background subtraction. In other examples, it is due to negative intensities corresponding to regions corrupted by glare that is not completely masked from the analysis.

FIG. 8 relates to step 110 of FIG. 1, segmenting the area represented in a sequence of images into regions based on measures of similarity between regions over the sequence. FIG. 8 shows a schematic flow diagram 802 depicting a robust region merging approach of segmentation according to an illustrative embodiment of the invention. One objective of the robust region merging approach is to take into account the "homogeneity" of data inside the different regions. While the region merging approach outlined in FIG. 6 relies essentially on the mean signal of each region to decide subsequent merging, the robust region merging approach outlined in FIG. 8 controls the maximum variability allowed inside each region. More specifically, the variance signal, $\sigma^2_w(k;t)$, associated with each region, k, is computed as in Equation (17):

$$\sigma^2_w(k;t) = \frac{1}{N_k}\sum_{(i,j)\in s_k}(w(i,j;t) - w(k;t))^2 \qquad (17)$$

$$= \frac{1}{N_k}\sum_{(i,j)\in s_k}w^2(i,j;t) - \left(\frac{1}{N_k}\sum_{(i,j)\in s_k}w(i,j;t)\right)^2,$$

where $w(k;t)$ is mean signal intensity of region k as expressed in Equation (10). The merging criterion is then the energy of the standard deviation signal, computed as in Equation (18):

$$\langle \sigma_w, \sigma_w \rangle = \sum_{t\in T}\sigma^2_w(k;t). \qquad (18)$$

Segmentation using the illustrative robust region merging approach begins at step 804 of the schematic flow diagram 802 of FIG. 8. In step 804 of FIG. 8, the variance signal, $\sigma^2_w(k;t)$, of Equation (17) is computed for each region k. Then variance signal energy, or the energy of the standard deviation signal as shown in Equation (18), is calculated for each region k. In step 806 of FIG. 8, the values of variance signal energy that are larger than a given threshold are sorted. This determines which regions can be merged, but not in which order the regions may be merged. In step 808 of FIG. 8, the sorted pairs are merged according to the increase in variance each merged pair would create, $\Delta_\sigma(k,l)$, given by Equation (19):

$$\Delta_\sigma(k, l) = \sum_{t \in T} \left( \sigma_w^2(k \cup l; t) - \frac{1}{2}\left[\sigma_w^2(k; t) + \sigma_w^2(l; t)\right] \right), \quad (19)$$

where k and l represent two neighboring regions to be merged. Thus, if a region can merge with more than one of its neighbors, it merges with the one that increases less the variance shown in Equation (19). Another neighbor may merge with the region in the next iteration, given that it still meets the fitting criterion with the updated region.

According to the illustrative embodiment, it is possible that a large region neighboring a small region will absorb the small region even when the regions have different signals. This results from the illustrative merging criterion being size-dependent, and the change in variance is small if the smaller region is merged into the larger region. According to a further embodiment, the methods of the invention apply an additional criterion as shown in step 807 of FIG. 8 prior to merging sorted pairs in step 808. In step 807, fitting values corresponding to the pairs of neighboring regions are checked against a threshold. The fitting values are determined as shown in Equation (11), used in the region-merging approach. According to the illustrative embodiment, a candidate pair of regions are not merged if its fitting value is below the threshold (e.g., if the two regions are too dissimilar). In the illustrative embodiment, the invention employs a fixed similarity criterion threshold of about $\phi_{kl}$=0.7. This value is low enough not to become the main criterion, yet the value is high enough to avoid the merging of regions with very different signals. However, other $\phi_{kl}$ values may be used without deviating from the scope of the invention.

In step 809 of FIG. 8, values of the variance signal are recalculated for pairs of neighboring regions containing an updated (newly-merged) region. According to an embodiment of the invention, variance signal values are not recalculated for pairs of neighboring regions whose regions are unchanged.

In step 810 of FIG. 8, the illustrative method of the invention determines whether the values of the variance signal energy for all regions are below a given variance threshold. If all values are below the threshold, the merging is complete 812. If not, the process beginning at step 806 is repeated, and values of variance signal energy of neighboring pairs of regions above the threshold are sorted.

Figure 9A:
FIG. 9A represents a segmentation mask produced using a robust region merging approach according to an illustrative embodiment of the invention.
Figure 9B:
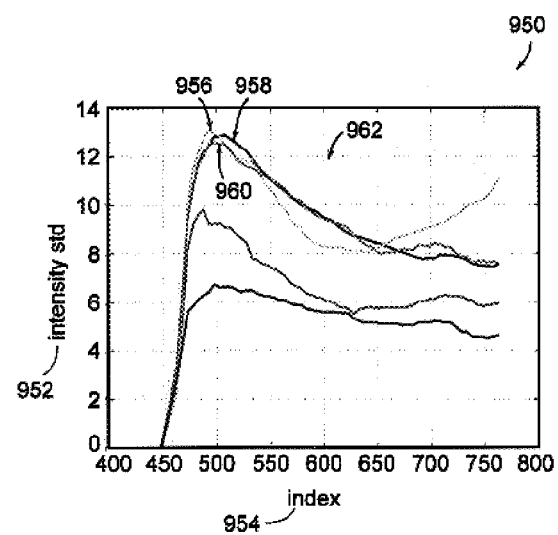
FIG. 9B shows a graph depicting mean variance signals of segmented regions represented in FIG. 9A as functions of time according to an illustrative embodiment of the invention.

FIGS. 9A and 9B illustrate step 112 of FIG. 1, relating images after segmentation. FIG. 9A depicts a segmentation mask 902 produced using the robust region merging segmentation technique discussed above for an exemplary aceto-whitening sequence. In the illustrative embodiment, the variance threshold used in step 810 of FIG. 8 to produce the segmentation mask 902 is 70. However, other variance thresholds may be employed without deviating from the scope of the invention. Each region has a different label, and is represented by a different color in the mask 902 to improve the contrast between neighboring regions. Other display techniques may be used to relate images of the sequence based on segmentation and/or based on the measure of similarity.

FIG. 9B shows a graph 950 depicting mean signal intensity 952 of segmented regions represented in FIG. 9A as functions of a time index 954 according to an illustrative embodiment of the invention. The color of each curve in FIG. 9B corresponds to the same-colored segment depicted in FIG. 9A. This is one way to visually relate a sequence of images using the results of segmentation.

According to the illustrative embodiment, the method observes data series 956, 958, 960, and 962 in FIG. 9B, whose signal intensities 952 increase more quickly than the other data series. The location of the four regions corresponding to these four data series are in FIG. 9A. In another embodiment, the method derives kinetic rate constants from each of the data series determined in FIG. 9B, and the regions having data series most closely matching kinetic rate constants of interest are identified. In another example, the method curve fits one or more data series to obtain a characterization of the mean signal intensities 952 of each data series as functions of time.

Figure 10:
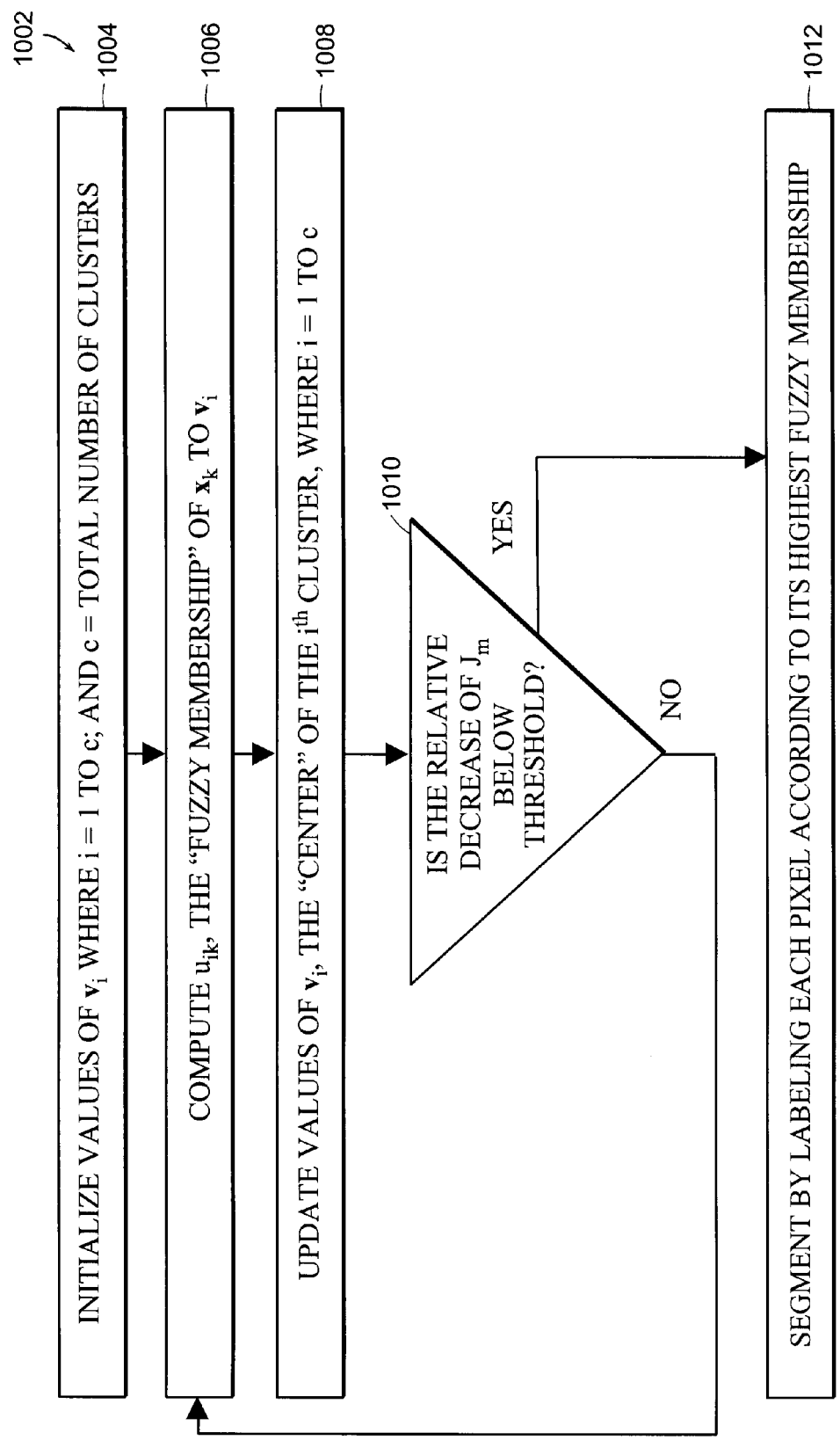
FIG. 10 is a schematic flow diagram depicting a clustering approach of segmentation according to an illustrative embodiment of the invention.

FIG. 10 relates to step 110 of FIG. 1, segmenting an area represented in a sequence of images into regions based on measures of similarity between regions over the sequence, according to one embodiment of the invention. FIG. 10 shows a schematic flow diagram 1002 depicting a segmentation approach based on the clustering of data, or more precisely, a "fuzzy c-means" clustering segmentation approach, used in an embodiment of the invention. An objective of this clustering approach is to group pixels into clusters with similar values. Unlike the region merging and robust region merging approaches above, the method does not merge regions based on their spatial relation to each other. In other words, two non-neighboring regions may be merged, depending on the criterion used.

Let $\mathbb{X}=\{x_1, \ldots, x_n\} \subset \mathbb{R}^d$ be a set of n d-dimensional vectors. An objective of clustering is to split $\mathbb{X}$ into c subsets, called partitions, that minimize a given functional, $J_m$. In the case of the fuzzy c-means, this functional is given by Equation (20):

$$J_m = \sum_{k=1}^{n} \sum_{i=1}^{c} (u_{ik})^m \|x_k - v_i\|^2, \quad (20)$$

where $v_i$ is the "center" of the $i^{th}$ cluster, $u_{ik} \in [0,1]$ is called the fuzzy membership of $x_k$ to $v_i$, with $$\sum_{i=1}^{c} u_{ik} = 1,$$

and $m \in [1,\infty]$ is a weighting exponent. The inventors have used m=2 in exemplary embodiments. The distance $\|\cdot\|$ is any inner product induced norm on $\mathbb{R}^d$. The minimization of $J_m$ as defined by Equation (20) leads to the following iterative system:

$$u_{ik} = \left( \sum_{j=1}^{c} \left( \frac{\|x_k - v_i\|}{\|x_k - v_j\|} \right)^{\frac{2}{m-1}} \right)^{-1}, \quad (21)$$

$$v_i = \frac{\sum_{k=1}^{n} (u_{ik})^m x_k}{\sum_{k=1}^{n} (u_{ik})^m}. \quad (22)$$

The distance, $\|x_k - v_j\|$, is based on the fitting function given in Equation (11). If it is assumed that similar signals are at a short distance from each other, then Equation (23) results:

$$\|x_k - v_i\| = \frac{1}{2}(1 - \varphi_{ki}), \quad (23)$$

where $\phi_{ki}$ is given by Equation (11).

Thus, in this embodiment, the segmentation begins at step 1004 of FIG. 10; and the method initializes values of $v_i$, where i=1 to c and c is the total number of clusters. In one embodiment, the method sets the initial value of $v_i$ randomly. In step 1006 of FIG. 10, the method calculates values of $u_{ik}$, the fuzzy membership of $x_k$ to $v_i$, according to Equation (21). In step 1008 of FIG. 10, the method updates values of $v_i$ according to Equation (22), using the previously determined value of $u_{ik}$. The algorithm converges when the relative decrease of the functional $J_m$ as defined by Equation (20) is below a predefined threshold, for instance, 0.001. Thus, in step 1010 of FIG. 10, an embodiment of the method determines whether the relative decrease of $J_m$ is below the threshold. If not, then the process beginning at step 1006 is repeated. If the relative decrease of $J_m$ is below the threshold, then the segmentation is completed by labeling each pixel according to its highest fuzzy membership, $$\text{e.g. } \underset{i \in \{1, \dots, c\}}{\text{maxind}} \{u_{ik}\}.$$

Some embodiments have more regions than clusters, since pixels belonging to different regions with similar signals can contribute to the same cluster.

Figure 11A:
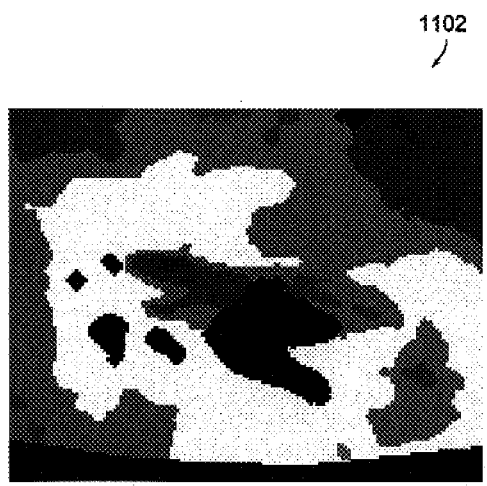
FIG. 11A represents a segmentation mask produced using a clustering approach according to an illustrative embodiment of the invention.
Figure 11B:
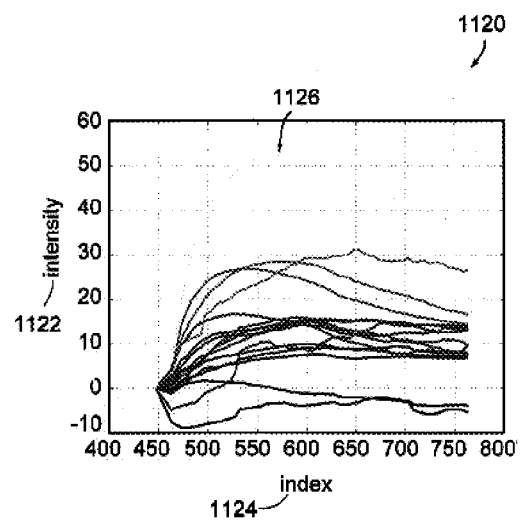
FIG. 11B shows a graph depicting mean signal intensities of segmented regions represented in FIG. 11A as functions of time according to an illustrative embodiment of the invention.

FIGS. 11A and 11B show an illustrative embodiment of the method at step 112 of FIG. 1. FIG. 11A depicts a segmentation mask 1102 produced using the clustering technique discussed above for an exemplary aceto-whitening sequence, according to the embodiment. The number of clusters, c, chosen in this embodiment is 3. There are more regions than clusters, since portions of some clusters are non-contiguous. The threshold for the relative decrease of $J_m$ in step 1010 of FIG. 10 is chosen as 0.001 in this embodiment. Each cluster has a different label and is represented by a different color in the mask 1102. Other embodiments employ other kinds of display techniques to relate images of the sequence based on segmentation and/or based on the measure of similarity.

FIG. 11B shows a graph 1120 depicting mean signal intensities 1122 of segmented regions represented in FIG. 11A as functions of a time index 1124 according to an illustrative embodiment of the invention. The color of each data series in FIG. 11B corresponds to the same-colored cluster depicted in FIG. 11A. The graph 1120 of FIG. 11B is one way to visually relate a sequence of images using the results of segmentation according to this embodiment. In this embodiment, the method identifies a cluster having a high initial rate of increase of signal intensity 1122 by observing data series 1126 in FIG. 11B, whose signal intensity increases more quickly than the other data series. Regions belonging to the same cluster have data series 1126 of the same color. In another embodiment, the method derives kinetic rate constants from each of the data series determined in FIG. 11B, and the regions having data series most closely matching kinetic rate constants of interest are identified. In another example, the method curve fits one or more data series to obtain characterization of the mean signal intensities 1122 of each data series as functions of time.

Figure 11C:
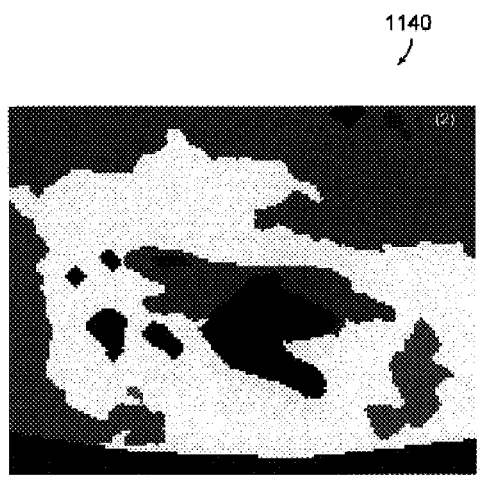
FIG. 11C represents a segmentation mask produced using a clustering approach according to an illustrative embodiment of the invention.
Figure 11D:
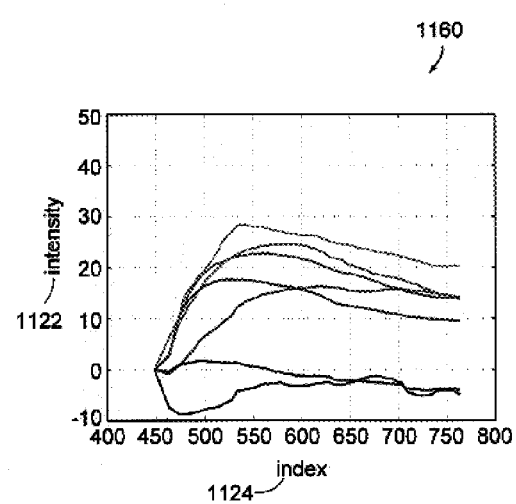
FIG. 11D shows a graph depicting mean signal intensities of segmented regions represented in FIG. 11C as functions of time according to an illustrative embodiment of the invention.

Similarly, FIGS. 11C and 11D illustrate an embodiment of the method at step 112 of FIG. 1, relating images after segmentation. FIG. 11C depicts a segmentation mask 1140 produced using the clustering technique for the exemplary aceto-whitening sequence in FIG. 11A, according to the embodiment. In FIG. 11C, however, the number of clusters, c, chosen is 2. Again, there are more regions than clusters, since portions of the same clusters are non-contiguous. The threshold for the relative decrease of $J_m$ in step 1010 of FIG. 10 is 0.001 for this embodiment.

Figure 12:
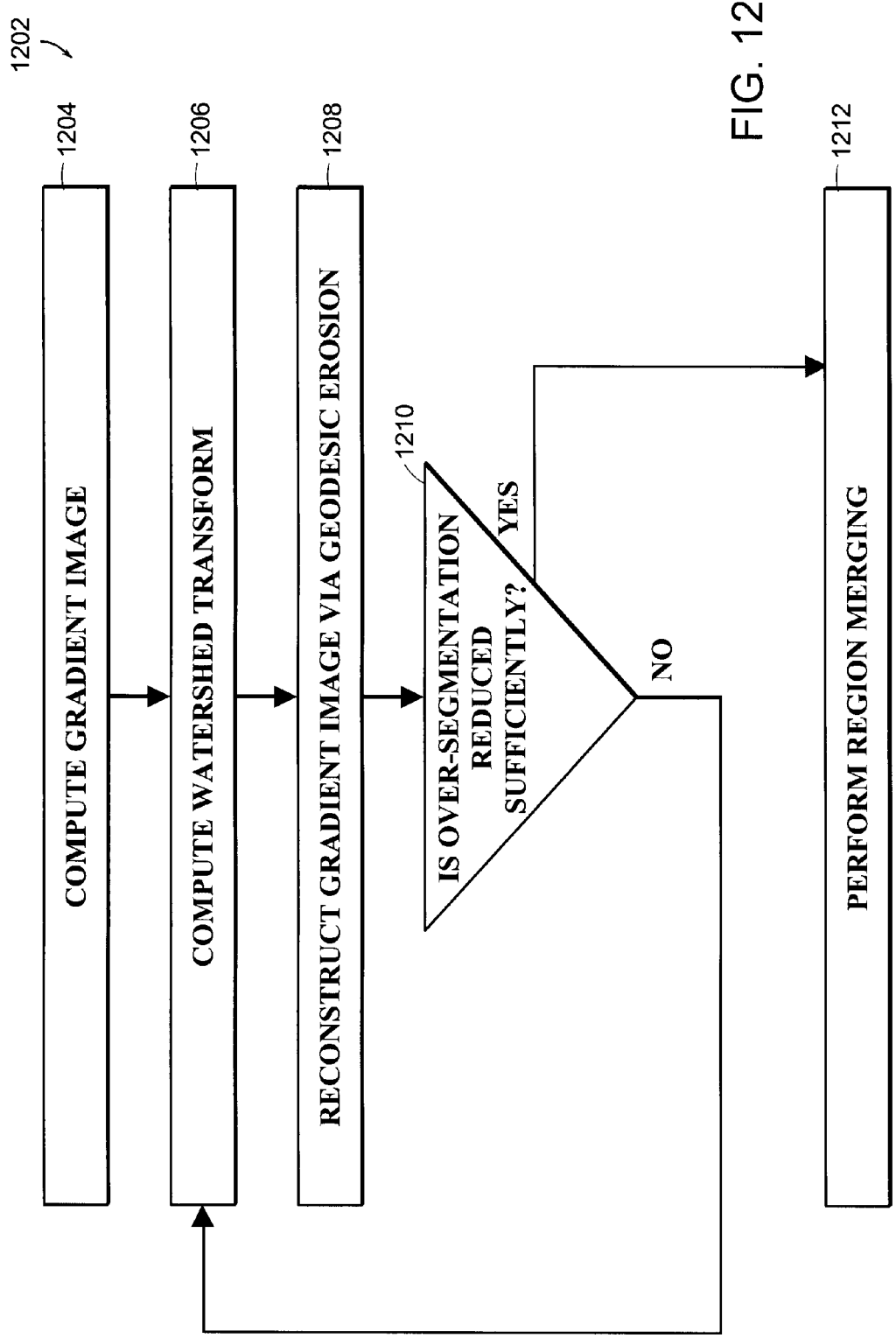
FIG. 12 is a schematic flow diagram depicting a watershed approach of segmentation according to an illustrative embodiment of the invention.

FIG. 12 relates to step 110 of FIG. 1, segmenting the area represented in a sequence of images into regions based on measures of similarity between regions over the sequence, according to an illustrative embodiment of the invention. In this embodiment, morphological techniques of segmentation are continued beyond filtering and pre-segmentation. FIG. 12 shows a schematic flow diagram 1202 depicting a hierarchical watershed approach of segmentation according to the illustrative embodiment.

In step 1204 of FIG. 12, the method computes a gradient image from Equations (14) and (15) according to the embodiment, which incorporates data from the entire sequence of images, as discussed above. The method segments data based on information from the entire sequence of images, not just one image. A watershed transform is applied to this gradient image in step 1206 of FIG. 12. Some embodiments apply first-in-first-out (FIFO) queues, sorted data, and other techniques to speed the performance of the watershed transform. Also, in some embodiments, the method applies a sigmoidal scaling function to the gradient image, prior to performing the watershed transform to enhance the contrast between whitish and reddish (dark) regions, which is particularly useful when analyzing images of a cervix. The catchment basins resulting from application of the watershed transform represent the segmented regions in this embodiment.

Figure 13:
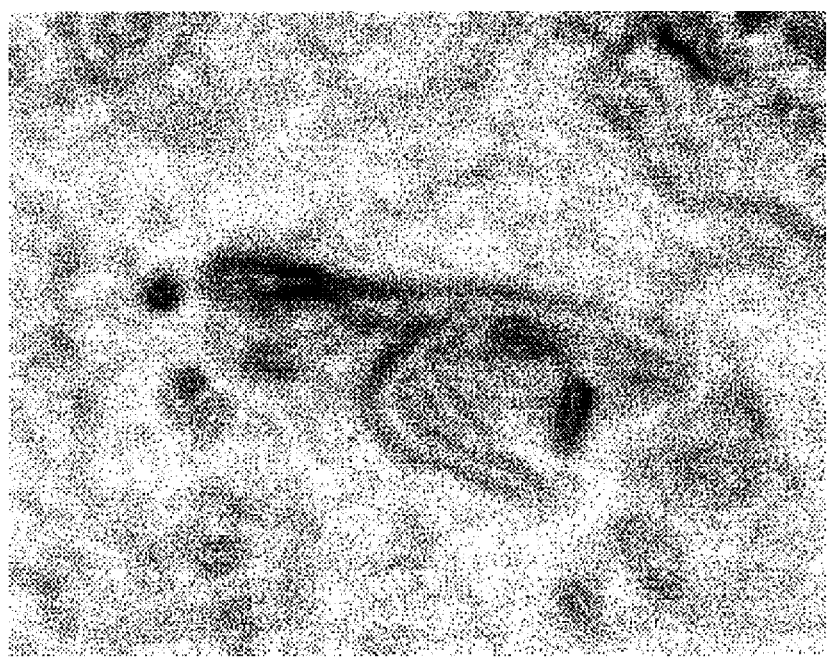
FIG. 13 represents a gradient image used in a watershed approach of segmentation according to an illustrative embodiment of the invention.

FIG. 13 shows a gradient image 1302 calculated from Equations (5) and (6) for an exemplary sequence of images, according to an embodiment of the invention.

According to an embodiment, the method at step 1208 of FIG. 12 constructs a new gradient image using geodesic reconstruction. Two different techniques of geodesic reconstruction which embodiments may employ include erosion and dilation. In step 1210 of FIG. 12, the method determines whether over-segmentation has been reduced sufficiently, according to this embodiment. If so, the segmentation may be considered complete, or one or more additional segmentation techniques may be applied, such as a region merging or robust region merging technique, both of which are discussed above. If over-segmentation has not been reduced sufficiently, the method calculates the watershed transform of the reconstructed gradient image as in step 1206, and the process is continued.

Certain embodiment methods use the hierarchical watershed to segment larger areas, such as large lesions or the background cervix. In some embodiments, the number of iterations is less than about 4 such that regions do not become too large, obscuring real details.

In some embodiments, the method performs one iteration of the hierarchical watershed, and continues merging regions using the robust region merging technique.

Figure 14A:
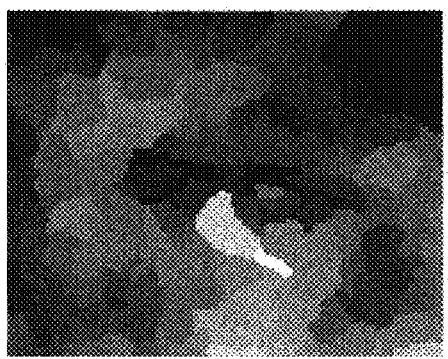
FIG. 14A represents a segmentation mask produced using a watershed approach according to an illustrative embodiment of the invention.
Figure 14B:
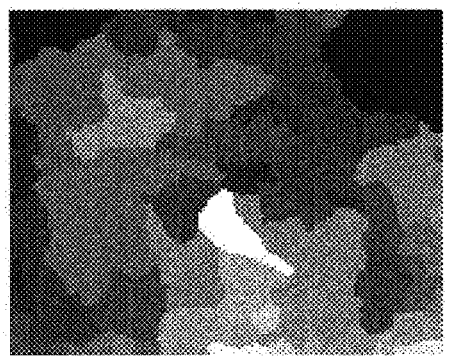
FIG. 14B represents a segmentation mask produced using a watershed approach according to an illustrative embodiment of the invention.
Figure 15A:
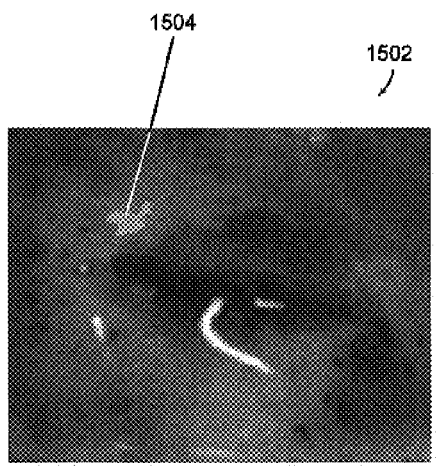
FIG. 15A represents a seed region superimposed on a reference image from a sequence of images, used in a region growing approach of segmentation according to an illustrative embodiment of the invention.
Figure 15B:
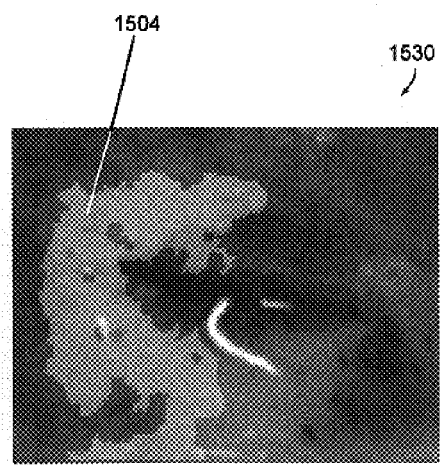
FIG. 15B represents the completed growth of the "seed region" of FIG. 15A using a region growing approach according to an illustrative embodiment of the invention.

FIGS. 14A and 14B show an illustrative embodiment of the method at step 112 of FIG. 1, relating images after segmentation. FIG. 14A depicts a segmentation mask 1402 produced using one iteration of the hierarchical watershed technique discussed above for an exemplary aceto-whitening sequence, according to the embodiment. Each region has a different label, and is represented by a different color in the mask 1402. FIG. 14B depicts a segmentation mask 1430 produced using two iterations of the hierarchical watershed technique discussed above for the exemplary aceto-whitening sequence, according to the embodiment. The segmentation mask 1430 in FIG. 14B, produced using two iterations, has fewer regions and is more simplified than the segmentation mask 1402 in FIG. 14A, produced using one iteration.

Other embodiments employ a "region growing technique" to performing step 110 of FIG. 1, segmenting an area represented in a sequence of images into regions based on measures of similarity between regions over the sequence. The region growing technique is different from the region merging and robust region merging techniques in that one or more initial regions, called seed regions, grow by merging with neighboring regions. The region merging, robust region merging, and region growing methods are each iterative. The region merging and region growing techniques each use the same fitting function to evaluate the similarity between signals from neighboring regions. In some embodiments of the region growing algorithm, the user manually selects seed regions. In other embodiments, the seed regions are selected in an automatic fashion. Hard criteria may be used to select areas that are of high interest and/or which behave in a certain way. In some embodiments, a user selects seed regions based on that user's experience. The region growing algorithm then proceeds by detecting similar regions and adding them to the set of seeds.

One embodiment of the invention is a combined technique using the region growing algorithm, starting with a grain image, followed by performing one iteration of the hierarchical watershed technique, and then growing the selected region according to the robust region merging algorithm.

In some embodiments, the segmentation techniques discussed herein are combined in various ways. In some embodiments, the method processes and analyzes data from a sequence of images in an aceto-whitening test, for instance, using a coarse-to-fine approach. In one embodiment, a first segmentation reveals large whitening regions, called background lesions, which are then considered as regions of interest and are masked for additional segmentation.

A second segmentation step of the embodiment may outline smaller regions, called foreground lesions. Segmentation steps subsequent to the second step may also be considered. As used here, the term "lesion" does not necessarily refer to any diagnosed area, but to an area of interest, such as an area displaying a certain whitening characteristic during the sequence. From the final segmentation, regions are selected for diagnosis, preliminary or otherwise; for further analysis; or for biopsy, for example. Additionally, the segmentation information may be combined with manually drawn biopsy locations for which a pathology report may be generated. In one illustrative embodiment, the method still applies the pre-processing procedures discussed herein above before performing the multi-step segmentation techniques.

Figure 16A:
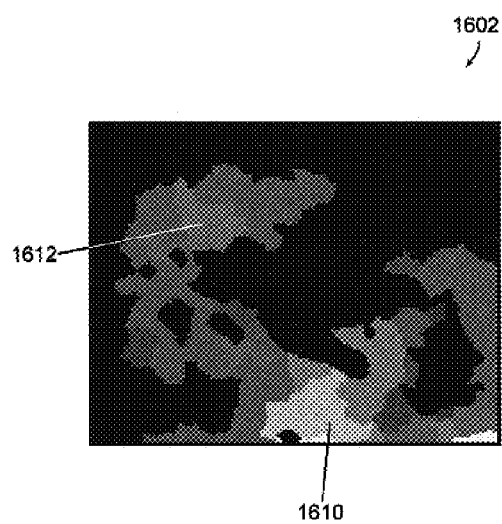
FIG. 16A represents a segmentation mask produced using a combined clustering approach and robust region merging approach according to an illustrative embodiment of the invention.

FIG. 16A shows a segmentation mask produced using a combined clustering approach and robust region merging approach for an exemplary aceto-whitening sequence, according to an illustrative embodiment of the invention. In the embodiment, the method performs pre-processing steps, including pre-segmenting pixels into grains using a watershed transform as discussed herein above. Then, the method applies the clustering technique to the sequence as discussed in FIG. 10, using c=3 clusters and $J_m$=0.001. This produces a "coarse" segmentation. From this coarse segmentation, the method selects a boomerang-shaped background lesion, corresponding to a large whitening region. The method masks out, or eliminates from further analysis, the remaining areas of the image frame.

Then, a robust region merging procedure is applied, as shown in FIG. 8, to the background lesion, according to the embodiment. Here, the method uses a similarity criterion of $\phi_{ki}$=0.7 in step 807 of FIG. 8, and a variance threshold of 120 in step 810 of FIG. 8. In this and other embodiments, regions less than 16 pixels large are removed. The resulting segmentation is shown in frame 1602 of FIG. 16A.

Figure 16B:
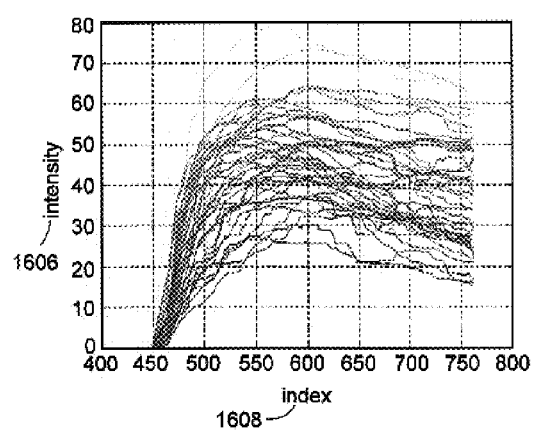
FIG. 16B shows a graph depicting mean signal intensities of segmented regions represented in FIG. 16A as functions of time according to an illustrative embodiment of the invention.

FIG. 16B shows a graph 1604 depicting mean signal intensity 1606 of segmented regions represented in FIG. 16A as functions of a time index 1608 according to an illustrative embodiment of the invention. The color of each curve in FIG. 16B corresponds to the same-colored segment depicted in FIG. 16A. Regions having a high initial rate of increase of signal intensity 1606 include regions 1610 and 1612, shown in FIG. 16A.

Figure 17A:
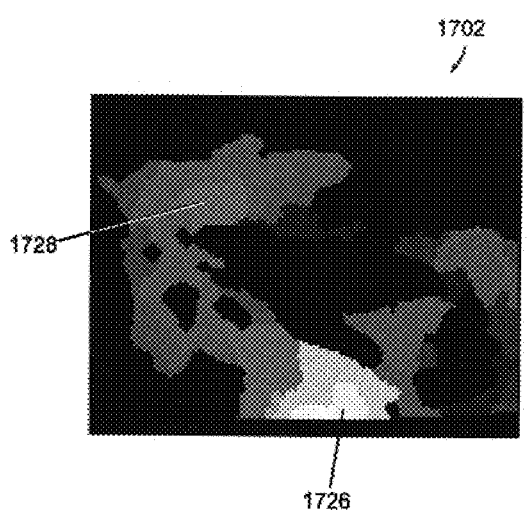
FIG. 17A represents a segmentation mask produced using a combined clustering approach and watershed technique according to an illustrative embodiment of the invention.

FIG. 17A represents a segmentation mask produced using a combined clustering approach and watershed approach for the exemplary aceto-whitening sequence of FIG. 16A, according to an illustrative embodiment of the invention. The method performs pre-processing steps, including the pre-segmenting of pixels into grains using a watershed transform as discussed herein above. Then, the method applies the clustering technique to the sequence as discussed in FIG. 10, using c=3 clusters and $J_m$=0.001. This produces a "coarse" segmentation. From this coarse segmentation, the method selects a boomerang-shaped background lesion, corresponding to a large whitening region. The method masks out remaining areas of the image frame.

Then, the method applies a hierarchical watershed segmentation procedure, as shown in FIG. 12. In this embodiment, the method computes one iteration of the watershed transform, then a region merging technique as per FIG. 6, using a fitting value threshold of 0.85 in step 610 of FIG. 6. Regions smaller than 16 pixels are removed. The resulting segmentation is shown in frame 1702 of FIG. 17A.

Figure 17B:
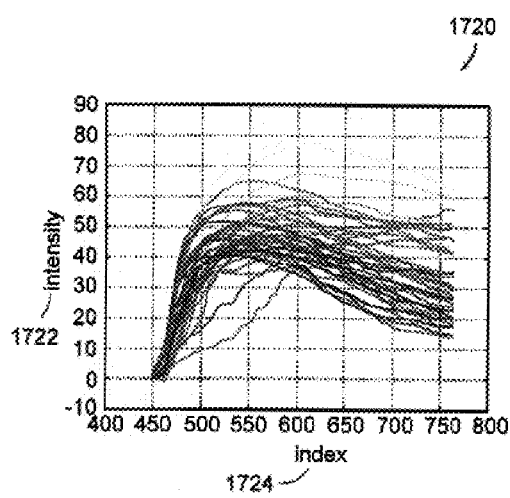
FIG. 17B shows a graph depicting mean signal intensities of segmented regions represented in FIG. 17A as functions of time according to an illustrative embodiment of the invention.

FIG. 17B shows a graph 1720 depicting mean signal intensity 1722 of segmented regions represented in FIG. 17A as functions of a time index 1724 according to an illustrative embodiment of the invention. The color of each curve in FIG. 17B corresponds to the same-colored segment depicted in FIG. 17A. Regions having a high initial rate of increase of signal intensity 1722 include regions 1726 and 1728, shown in FIG. 17A.

Figure 18A:
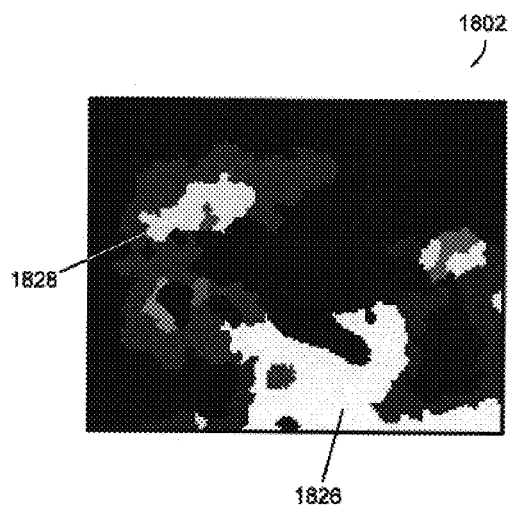
FIG. 18A represents a segmentation mask produced using a two-part clustering approach according to an illustrative embodiment of the invention.

FIG. 18A represents a segmentation mask produced using a two-step clustering approach for the exemplary acetowhitening sequence of FIG. 16A, according to an illustrative embodiment of the invention. The method performs pre-processing steps, including pre-segmenting pixels into grains using a watershed transform as discussed herein above. Then, the method applies a clustering technique to the sequence as discussed in FIG. 10, using c=3 clusters and $J_m$=0.001. This produces a "coarse" segmentation. From this coarse segmentation, the method selects a boomerang-shaped background lesion, corresponding to a large whitening region. The method masks out the remaining areas of the image frame from further analysis.

Then, the method applies a second clustering procedure, as shown in FIG. 10, to the background lesion. Here again, the method uses c=3 clusters and $J_m$=0.001. Regions less than 16 pixels large are removed. This produces a foreground lesion, shown in frame 1802 of FIG. 18A.

Figure 18B:
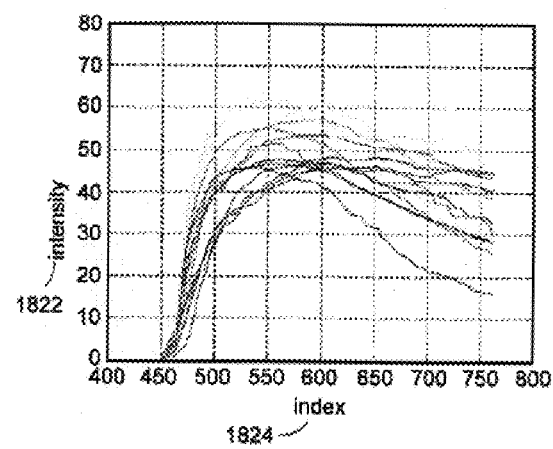
FIG. 18B shows a graph depicting mean signal intensities of segmented regions represented in FIG. 18A as functions of time according to an illustrative embodiment of the invention.

FIG. 18B shows a graph 1820 depicting mean signal intensity 1822 of segmented regions represented in FIG. 18A as functions of a time index 1824 according to an illustrative embodiment of the invention. The color of each curve in FIG. 18B corresponds to the same-colored cluster depicted in FIG. 18A. Regions having a high initial rate of increase of signal intensity 1822 include regions 1828 and 1826, shown in FIG. 18A.

Figure 19:
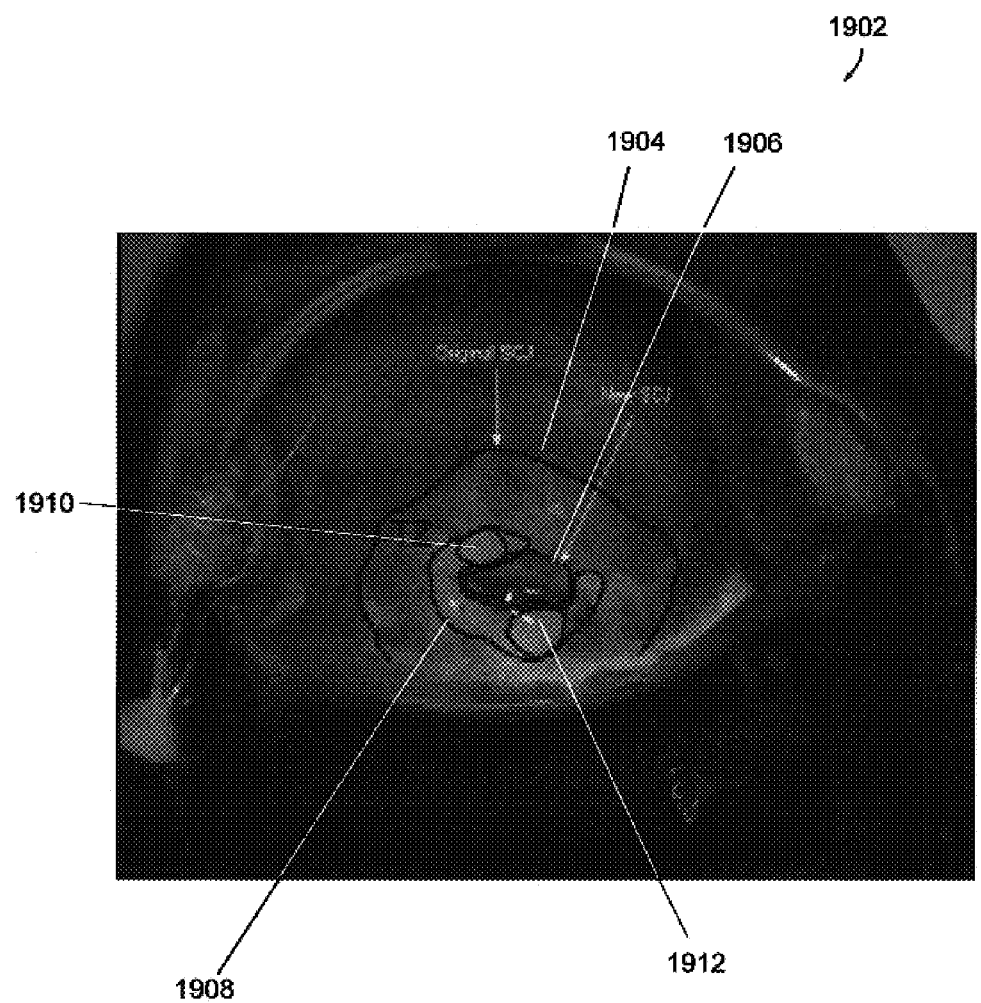
FIG. 19 depicts the human cervix tissue of FIG. 2A with an overlay of manual doctor annotations made after viewing an image sequence.

FIG. 19 depicts the human cervix tissue of FIG. 2A with an overlay of manual doctor annotations made after viewing the exemplary aceto-whitening image sequence discussed herein above. Based on her viewing of the sequence and on her experience with the aceto-whitening procedure, the doctor annotated regions with suspicion of pathology 1904, 1906, 1908, 1910, and 1912. The doctor did not examine results of any segmentation analysis prior to making the annotations. Regions 1910 and 1912 were singled out by the doctor as regions with the highest suspicion of pathology.

Figures 20A, 20B:
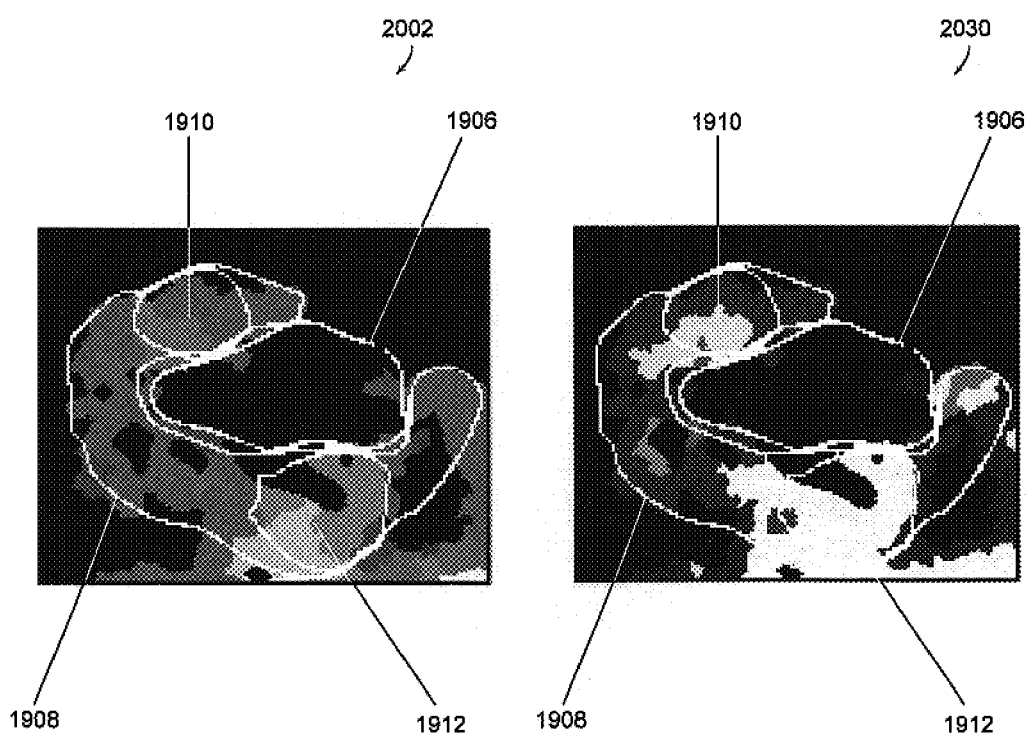
FIG. 20A is a representation of a segmentation mask produced using a combined clustering approach and robust region merging approach with a correspondingly-aligned overlay of the manual doctor annotations of FIG. 19, according to an embodiment of the invention.
FIG. 20B is a representation of a segmentation mask produced using a combined clustering approach and morphological technique with a correspondingly-aligned overlay of the manual doctor annotations of FIG. 19, according to an embodiment of the invention.

FIG. 20A is a representation of a segmentation mask produced using a combined clustering approach and robust region merging approach as discussed above and as shown in FIG. 16A, according to an illustrative embodiment of the invention. The segmentation mask in FIG. 20A, however, is shown with a correspondingly-aligned overlay of the manual doctor annotations of FIG. 19. FIG. 20B is a representation of a segmentation mask produced using a combined clustering approach and watershed technique as discussed above and shown in FIG. 18A. The segmentation mask in FIG. 20B, however, is shown with a correspondingly-aligned overlay of the manual doctor annotations of FIG. 19, according to an embodiment of the invention.

Areas 1912 and 1910 in FIGS. 20A and 20B correspond to the doctor's annotations of areas of high suspicion of pathology. In the segmentation masks produced from the combined techniques of both FIGS. 20A and 20B, these areas (1912 and 1910) correspond to regions of rapid, intense whitening. In the doctor's experience, areas of rapid, intense whitening correspond to areas of suspicion of pathology. Thus, the techniques discussed herein provide a method of determining a tissue characteristic, namely, the presence or absence of a suspicion of pathology. Certain embodiments of the invention use the techniques in addition to a doctor's analysis or in place of a doctor's analysis. Certain embodiments use combinations of the methods described herein to produce similar results.

Some embodiments of the invention for applications other than the analysis of acetowhitening tests of cervical tissue also use various inventive analysis techniques as described herein. A practitioner may customize elements of an analysis technique disclosed herein, based on the attributes of her particular application, according to embodiments of the invention. For instance, the practitioner may choose among the segmentation techniques disclosed herein, depending on the application for which she intends to practice embodiments of the inventive methods. By using the techniques described herein, it is possible to visually capture all the frames of a sequence at once and relate regions according to their signals over a period of time.

Certain embodiments of the invention methods analyze more complex behavior. Some embodiments segment the image plane of a sequence of images, then feature-extract the resulting mean intensity signals to characterize the signals of each segmented region. Examples of feature extraction procedures include any number of curve fitting techniques or functional analysis techniques used to mathematically and/or statistically describe characteristics of one or more data series. In some embodiments, these features are then used in a manual, automated, or semi-automated method for the classification of tissue.

For example, in certain embodiments, the method classifies a region of cervical tissue either as "high grade disease" tissue, which includes Cervical Intraepithelial Neoplasia II/III (CIN II/III), or as "not high grade disease" tissue, which includes normal squamous (NED—no evidence of disease), metaplasia, and CIN I tissue. The classification for a segmented region may be within a predicted degree of certainty using features extracted from the mean signal intensity curve corresponding to the region. In one embodiment, this classification is performed for each segmented region in an image plane to produce a map of regions of tissue classified as high grade disease tissue. Other embodiments make more specific classifications and distinctions between tissue characteristics, such as distinction between NED, metaplasia, and CIN I tissue.

Figure 21A:
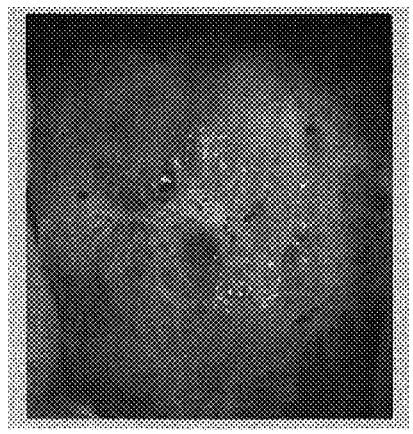
FIG. 21A depicts a reference image of cervical tissue of a patient from a sequence of images obtained during an acetowhitening test according to an illustrative embodiment of the invention.
Figure 21B:
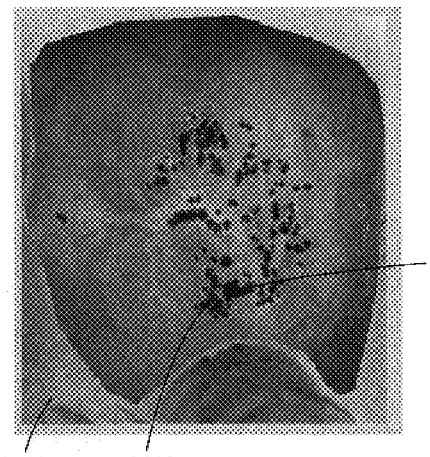
FIG. 21B depicts an image from the sequence of FIG. 21A after applying a manual mask, accounting for glare, and accounting for chromatic artifacts according to an illustrative embodiment of the invention.
Figure 21C:
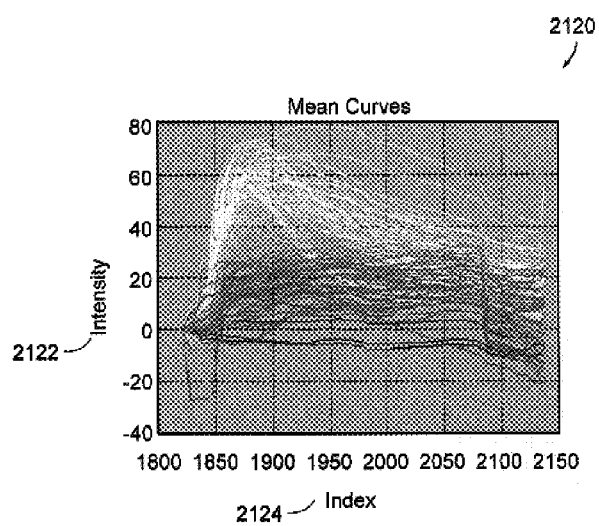
FIG. 21C shows a graph depicting mean signal intensities of segmented regions for the sequence of FIG. 21A determined using a clustering segmentation approach according to an illustrative embodiment of the invention.

FIG. 21A, FIG. 21B, FIG. 21C, and FIG. 21D depict steps in the classification of regions of tissue in a sequence of images obtained during an acetowhitening procedure performed on a patient with high grade disease according to an illustrative embodiment of the invention. FIG. 21A depicts a reference image 2102 of cervical tissue of the patient from a sequence of images obtained during the acetowhitening test. FIG. 21B is a representation 2106 of the reference image 2102 of FIG. 21A after applying a manual mask, accounting for glare, and accounting for chromatic artifacts as discussed herein according to an illustrative embodiment of the invention. For example, areas such as areas 2110 and 2112 of FIG. 21B have been masked for glare and chromatic effects, respectively, using techniques as discussed herein. FIG. 21C shows a graph 2120 depicting mean signal intensities 2122 of segmented regions for the sequence of FIG. 21A as functions of a time index 2124 and as determined using the clustering segmentation approach depicted in the schematic flow diagram 1002 of FIG. 10 and as discussed herein according to an illustrative embodiment of the invention.

It was desired to classify each of the segmented regions as either "indicative of high grade disease" or "not indicative of high grade disease." Thus, an embodiment of the invention extracted specific features from each of the mean signal intensity data series depicted in the graph 2120 of FIG. 21C, and used these features in a classification algorithm.

A classification algorithm was designed using results of a clinical study. In the study, mean signal intensity curves were determined using sequences of images from acetowhitening tests performed on over 200 patients. The classification algorithm may be updated according to an embodiment of the invention upon conducting further or different clinical testing. The present algorithm was based upon two feature parameters extracted from each of certain mean signal intensity data series corresponding to segmented regions of the image sequences for which biopsies were performed. These two feature parameters are as follows:

1. X is the slope of a curve (here, a polynomial curve) fitted to the mean signal intensity data series of a segmented region at the time corresponding to 235 seconds after application of the acetic acid (M235); and
2. Y is the slope of the polynomial curve at the time corresponding to an intensity that is −16 dB from the maximum intensity (about 45% of the maximum mean signal intensity) on the decaying side of the polynomial curve (−16 dB slope).

The choice of the feature parameters X and Y above was made by conducting a Discrimination Function (DF) analysis of the data sets from the clinical study. A wide range of candidate feature parameters, including X and Y, were tested. X and Y provided a classification algorithm having the best accuracy.

A jackknifed classification matrix linear discriminant analysis was performed on the extracted features X and Y corresponding to certain of the mean signal intensity curves from each of the clinical tests. The curves used were those corresponding to regions for which tissue biopsies were performed. From the linear discriminant analysis, it was determined that a classification algorithm using the discriminant line shown in Equation (24) results in a diagnostic sensitivity of 88% and a specificity of 88% for the separation of CIN II/III (high grade disease) from the group consisting of normal squamous (NED), metaplasia, and CIN I tissue (not high grade disease):

$$Y = -0.9282X - 0.1348. \quad (24)$$

Varying the classification model parameters by as much as 10% yields very similar model outcomes, suggesting the model features are highly stable.

Figure 21D:
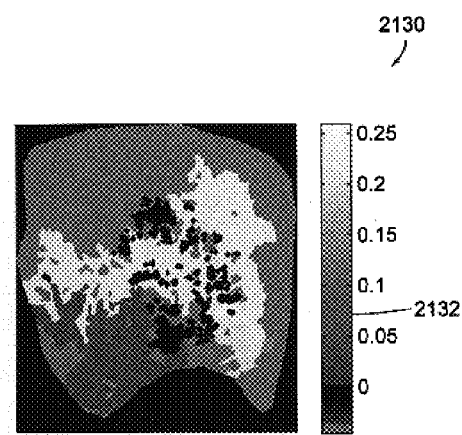
FIG. 21D represents a map of regions of tissue as segmented in FIG. 21C classified as either high grade disease tissue or not high grade disease tissue using a classification algorithm according to an illustrative embodiment of the invention.

FIG. 21D represents a map 2130 of regions of tissue as segmented in FIG. 21C classified as either high grade disease tissue or not high grade disease tissue using the classification algorithm of Equation (24). This embodiment determined this classification for each of the segmented regions by calculating X and Y for each region and determining whether the point (X,Y) falls below the line of Equation (24), in which case the region was classified as high grade disease, or whether the point (X,Y) falls above the line of Equation (24), in which case the region was classified as not high grade disease. The embodiment draws further distinction depending on how far above or below the line of Equation (24) the point (X,Y) falls. The map 2130 of FIG. 21D indicates segmented regions of high grade disease as red, orange, and yellow, and regions not classifiable as high grade disease as blue. The index 2132 reflects how far the point (X,Y) of a given segment falls below the line of Equation (24). Other embodiments include those employing other segmentation techniques as described herein. Still other embodiments include those employing different classification algorithms, including those using feature parameters other than X and Y, extracted from mean signal data series corresponding to segmented regions.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of locating a portion of tissue with a characteristic of interest, the method comprising the steps of:
   (a) characterizing an acetowhitening signal from a temporal sequence of images of a tissue following application of a chemical agent to the tissue, wherein the chemical agent comprises acetic acid;
   (b) analyzing the acetowhitening signal to determine a measure of similarity between two selected regions of the tissue, the measure of similarity indicating how similarly tissue in each region responds to the chemical agent, and grouping the two selected regions if the measure of similarity is larger than a given threshold, wherein the step of determining the measure of similarity comprises, for each of the two selected regions, averaging data corresponding to pixels within the region at each of a plurality of time steps to obtain a mean signal for the region, then quantifying the similarity between the two resulting, mean signals;
   (c) repeating step (b), thereby differentiating regions according to how tissue in each region responds to the chemical agent; and
   (d) locating a portion of the tissue with a characteristic of interest, the located portion corresponding to at least one of the differentiated regions.

2. The method of claim 1, wherein step (b) further comprises merging the two selected regions into a single region if the measure of similarity satisfies a predetermined criterion.

3. The method of claim 2, wherein steps (b) and (c) together comprise iteratively segmenting an area of the tissue into regions according to evolution of mean intensity of each region following application of the chemical agent.

4. The method of claim 1, wherein step (c) comprises repeating step (b) for each of a plurality of pairs of selected regions.

5. The method of claim 1, wherein the measure of similarity indicates a similarity in evolution of mean intensity of each region following application of the chemical agent.

6. The method of claim 1, wherein step (b) comprises computing an N-dimensional dot product of mean signal intensities of the two selected regions.

7. The method of claim 1, wherein the chemical agent further comprises a member selected from the group consisting of formic acid, propionic acid, butyric acid, Lugol's iodine, Shiller's iodine, methylene blue, toluidine blue, and indigo carmine.

8. The method of claim 1, further comprising the step of:
   (e) determining a condition of the located portion.

9. The method of claim 8, wherein the condition comprises a member selected from the group consisting of normal squamous tissue, metaplasia, CIN I, CIN II, CIN III, and CIN II/III.

10. The method of claim 8, wherein step (e) comprises determining a condition of the located portion based at least in part on evolution of mean intensity of the located portion.

11. The method of claim 8, wherein step (e) further comprises obtaining a biopsy specimen within the located portion prior to determining the condition of the located portion.

12. The method of claim 8, wherein the condition comprises a member selected from the group consisting of CIN II, CIN III, and CIN II/III.

13. The method of claim 1, wherein the characteristic of interest is a suspicion of pathology.

14. The method of claim 1, wherein the tissue comprises cervical tissue.

15. The method of claim 1, wherein the tissue comprises at least one member selected from the group consisting of epithelial tissue, colorectal tissue, skin, and uterine tissue.

16. The method of claim 1, further comprising the step of illuminating the tissue using a white light source, a UV light source, or both.

17. A method of differentiating regions of a tissue, the method comprising the steps of:
(a) accessing a temporal sequence of images of a tissue following application of a chemical agent to the tissue; and
(b) creating a segmentation mask that represents an image plane divided into regions according to how similarly tissue in each region responds to the chemical agent, wherein step (b) comprises analyzing an acetowhitening signal to determine a measure of similarity between two selected regions of the tissue, the measure of similarity indicating how similarly tissue in each region responds to the chemical agent, and grouping the two selected regions if the measure of similarity is larger than a given threshold, wherein the step of determining the measure of similarity comprises, for each of the two selected regions, averaging data corresponding to pixels within the region at each of a plurality of time steps to obtain a mean signal for the region, then quantifying the similarity between the two resulting mean signals.

18. The method of claim 17, wherein the chemical agent comprises a member selected from the group consisting of acetic acid, formic acid, propionic acid, butyric acid, Lugol's iodine, Shiller's iodine, methylene blue, toluidine blue, and indigo carmine.

19. The method of claim 17, wherein the chemical agent comprises acetic acid.

20. The method of claim 17, further comprising the step of:
(c) locating a portion of the tissue with a characteristic of interest, the located portion corresponding to at least one of the differentiated regions.

21. The method of claim 20, further comprising the step of:
(d) determining a condition of the located portion.

22. The method of claim 21, wherein the condition comprises a member selected from the group consisting of normal squamous tissue, metaplasia, CIN I, CIN II, CIN III, and CIN II/III.

23. The method of claim 21, wherein the condition comprises a member selected from the group consisting of CIN II, CIN III, and CIN II/III.

24. The method of claim 17, wherein the tissue comprises cervical tissue.

25. The method of claim 17, wherein the tissue comprises at least one member selected from the group consisting of epithelial tissue, colorectal tissue, skin, and uterine tissue.

26. The method of claim 17, wherein the step of creating the segmentation mask comprises analyzing an acetowhitening signal characterized from the temporal sequence of images, wherein the chemical agent comprises acetic acid.

27. A system for differentiating regions of a tissue, the system comprising:
a light source that illuminates a tissue;
a camera that obtains a temporal sequence of images of the tissue following application of a chemical agent to the tissue, the chemical agent comprising acetic acid; and
software that performs the steps of:
(i) characterizing an acetowhitening signal from temporal sequence of images;
(ii) analyzing the acetowhitening signal to determining a measure of similarity between two selected regions of the tissue, the measure of similarity indicating how similarly tissue in each region responds to the chemical agent, and grouping the two selected regions if the measure of similarity is larger than a given threshold, wherein the step of determining the measure of similarity comprises, for each of the two selected regions, averaging data corresponding to pixels within the region at each of a plurality of time steps to obtain a mean signal for the region, then quantifying the similarity between the two resulting mean signals; and
(iii) repeating step (ii), thereby differentiating regions according to how tissue in each region responds to the chemical agent.

28. The system of claim 27, wherein the chemical agent further comprises a member selected from the group consisting of formic acid, propionic acid, butyric acid, Lugol's iodine, Shiller's iodine, methylene blue, toluidine blue, and indigo carmine.

29. The system of claim 27, wherein the software further performs the step of:
(c) locating a portion of the tissue with a characteristic of interest, the located portion corresponding to at least one of the differentiated regions.

30. The system of claim 29, further comprising the step of:
(d) determining a condition of the located portion.

31. The system of claim 30, wherein the condition comprises a member selected from the group consisting of normal squamous tissue, metaplasia, CIN I, CIN II, CIN III, and CIN II/III.

32. The system of claim 30, wherein the condition comprises a member selected from the group consisting of CIN II, CIN III, and CIN II/III.

33. The system of claim 27, wherein the tissue comprises cervical tissue.

34. The system of claim 27, wherein the tissue comprises at least one member selected from the group consisting of epithelial tissue, colorectal tissue, skin, and uterine tissue.

* * * * *